(12) United States Patent
Suzuki et al.

(10) Patent No.: US 10,918,726 B2
(45) Date of Patent: Feb. 16, 2021

(54) CARBOSILANE DENDRIMER AND AGGREGATABLE CARRIER OBTAINED USING SAID DENDRIMER FOR DRUG DELIVERY SYSTEM

(71) Applicants: Quarrymen & Co. Inc., Tokyo (JP); Saitama University, Saitama (JP)

(72) Inventors: Miho Suzuki, Sitama (JP); Ken Hatano, Saitama (JP); Shojiro Yoshida, Saitama (JP); Yasuhiro Yamashita, Tokyo (JP)

(73) Assignees: QUARRYMEN & Co. Inc., Tokyo (JP); Saitama University, Saitama (JP)

(*) Notice: Subject to any disclaimer, the term of this patent is extended or adjusted under 35 U.S.C. 154(b) by 0 days.

(21) Appl. No.: 15/606,334

(22) Filed: May 26, 2017

(65) Prior Publication Data

US 2017/0281782 A1 Oct. 5, 2017

Related U.S. Application Data

(63) Continuation of application No. PCT/JP2015/083622, filed on Nov. 30, 2015.

(30) Foreign Application Priority Data

Nov. 28, 2014 (JP) .................................. 2014-242218

(51) Int. Cl.
| | |
|---|---|
| A61K 47/42 | (2017.01) |
| A61K 47/24 | (2006.01) |
| A61K 38/00 | (2006.01) |
| A61K 9/10 | (2006.01) |
| C08G 83/00 | (2006.01) |
| A61K 9/00 | (2006.01) |
| A61K 9/107 | (2006.01) |
| A61K 31/7088 | (2006.01) |
| A61K 38/17 | (2006.01) |
| A61K 38/22 | (2006.01) |
| A61K 39/395 | (2006.01) |

(52) U.S. Cl.
CPC ............ *A61K 47/42* (2013.01); *A61K 9/0019* (2013.01); *A61K 9/10* (2013.01); *A61K 9/107* (2013.01); *A61K 31/7088* (2013.01); *A61K 38/00* (2013.01); *A61K 38/1732* (2013.01); *A61K 38/22* (2013.01); *A61K 39/395* (2013.01); *A61K 47/24* (2013.01); *C08G 83/003* (2013.01)

(58) Field of Classification Search
CPC ....... A61K 47/42; A61K 9/107; C08G 83/003
See application file for complete search history.

(56) References Cited

U.S. PATENT DOCUMENTS

2012/0277158 A1    11/2012 Castaigne et al.

FOREIGN PATENT DOCUMENTS

| | | |
|---|---|---|
| EP | 1655022 A1 | 5/2006 |
| EP | 1655038 A1 | 5/2006 |
| JP | 2001-206885 A | 7/2001 |
| JP | 2005-120068 A | 5/2005 |
| JP | 2007-001923 A | 1/2007 |
| JP | 2007-238860 A | 9/2007 |
| JP | 2009-046413 A | 3/2009 |
| JP | 2011-063587 A | 3/2011 |
| JP | 2011063587 A * | 3/2011 |
| JP | 2013-082635 A | 5/2013 |
| JP | 2014-073975 A | 4/2014 |
| JP | 5629888 B2 | 11/2014 |
| WO | 2005/011632 A1 | 2/2005 |
| WO | 2005/011633 A1 | 2/2005 |
| WO | 2011041897 A1 | 4/2011 |
| WO | 2011050178 A2 | 4/2011 |

OTHER PUBLICATIONS

Aizawa, H. et al. "A carbosilane dendrimer and a silacyclopentadiene analog carrying peripheral lactoses as drug-delivery systems" Bioorganic & Medicinal Chemistry Letters 22 (2012) 3564-3566 (Year: 2012).*
Hatano, K. et al. "Fluorescence quenching detection of peanut agglutinin based on photoluminescent silole-core carbosilane dendrimer peripherally functionalized with lactose" Tetrahedron Letters 50 (2009) 5816-5819 (Year: 2009).*
Hiroaki Aizawa et al., "A carbosilane dendrimer and a silacyclopentadiene analog carrying peripheral lactoses as drug-delivery systems", Bioorganic & Medicinal Chemistry Letters, Pergamon, Amsterdam, NL, vol. 22, No. 10, Mar. 7, 2012, pp. 3564-3566. (cited in the Jun. 11, 2018 Search Report issued for EP15863638.1).
Search Report dated Jun. 11, 2018, issued for the corresponding European patent application No. 15863638.1.
Yuning Hong et al., "Aggregation-induced emission: phenomenon, mechanism and applications," Chem Comm, 2009, pp. 4332-4353.
International Search Report dated Jan. 12, 2016, issued for PCT/JP2015/083622.

* cited by examiner

*Primary Examiner* — Andres S Rosenthal
(74) *Attorney, Agent, or Firm* — Locke Lord LLP; James E. Armstrong, IV; Nicholas J. DiCeglie, Jr.

(57) ABSTRACT

The object of the present invention is to provide an aggregatable carrier material for drug delivery system and a micelle formed thereof. The present invention provides an aggregatable carrier material for drug delivery system, which is formed by utilizing the reaction between thiol group and alkyl halide. It is formed by using carbosilane dendrimers containing silole and labeled proteins such as green fluorescent protein in aqueous solvent or in mixed solvent of the aqueous solvent and organic solvent. The micelle composed of the material may incorporate compounds having a variety of molecular weight and biopolymers in the aqueous solvent.

9 Claims, 11 Drawing Sheets

Specification includes a Sequence Listing.

Scheme 2

CARBOSILANE DENDRIMER AND AGGREGATABLE CARRIER OBTAINED USING SAID DENDRIMER FOR DRUG DELIVERY SYSTEM

SEQUENCE LISTING

The instant application contains a Sequence Listing which has been submitted in ASCII format via EFS-Web and is hereby incorporated by reference in its entirety. Said ASCII copy, created on Apr. 24, 2020, is named P15SU005PCT ST25.txt and is 26,486 bytes in size.

TECHNICAL FIELD

The present invention relates to carbosilane dendrimer which is available for drug delivery system, and aggregatable carrier for drug delivery system.

BACKGROUND ART

Nowadays, a variety of disease treatment drug have been developed; especially, biopolymers such as antibody, peptide aptamer and nucleic acid have received attracted attention as next-generation drugs. The biopolymer should be handled differently from conventional drugs comprising a low molecular weight compound as active ingredient in various points such as quality control in manufacturing processes, storage of pharmaceutical preparations, and administration methods.

In general, amounts of the active ingredients to be delivered to target sites affects to response rate, when a pharmaceutical preparation is administered, depending on both of the disease to be treated and properties of the drug. Particularly, it is known that the problem that antibody produced depending on a dosage form at the time of administration reduced the efficacy of the administered drug and therapeutic effect, when the drug comprising the biopolymer as active ingredient is administered.

Therefore, a variety of drug delivery systems (DDS: drug delivery system) have been developed actively as methods for delivering the pharmaceutical preparation to the target site properly. As the carrier for DDS, for example, there are mentioned such as liposome, plastic beads and the like. As the pharmaceutical preparation using such a carrier used for DDS, for example, there are reported those composed of a liposome, to which a ligand specifically binds to a localized molecule in the target site (see patent documents 1 and 2); the liposome or synthetic polymer beads, on which N-acetyl glucosamine or other sugars are exposed (see patent documents 3 and 4), micelles to which antibodies are bound (see patent document 5), and the like.

Also, the carrier utilizing dendrimer having micelle structure is developed (see patent documents 6, 7 and 8). The term, Dendrimer, is a generic word showing dendritic polymer compound has regularly branched structure, of which origin is Greek term "dendra" (trees). Several dendrimer molecules assemble to be spherical form having a nanometer scale space in its inside. Then, since the molecules are incorporated so as to show various functional groups in the space, it has higher flexibility of design. Therefore, currently, various new dendrimers are been developed actively in the field of nanotechnology.

Dendrimer may be used as the carrier for DDS or the molecular sensor, which responds to external stimulation in biological system. Heretofore, in order to prevent and/or medicate a disease caused by viral or bacterial infections, for example, the carrier utilizing dendrimer has been developed (see patent document 9)

On the other hand, it is known that the dendrimer having silole group shows AIE (aggregation-induced emission) usually to generate fluorescence emission. Here, the term, AIE, which is defined as a phenomenon that the mutually aggregated light-emitting compounds gives high-efficient light emission after they are irradiated by the light with certain wavelength (See, non-patent document 1). However, it is not known that the similar emission occurs, after the compound is bound to the fluorescent protein.

PRIOR ART

Patent Document

[Patent Document 1] WO2005/011632
[Patent Document 2] WO2005/011633
[Patent Document 3] JP2007-1923 A
[Patent Document 4] JP2009-46414 A
[Patent Document 5] JP2014-73975 A
[Patent Document 6] JP2001-206885 A
[Patent Document 7] JP2005-120068 A
[Patent Document 8] JP2007-238860 A
[Patent Document 9] JP562988 B Non Patent Document

[Non Patent Document 1]
Chem Commun (Camb). 2009 Aug. 7; (29):4332-53. doi: 10.1039/b904665h. Epub 2009 May 13

SUMMARY OF THE INVENTION

Problem to be Solved by the Invention

As described above, the study of the carrier for DDS is progressed enthusiastically; however, it is almost impossible to transport the biopolymers effectively without lacking their properties. Concretely, per so among the administration routes to the living body, the biopolymer as the active ingredient is neither delivered to intestine nor absorbed therefrom, unless the carrier is prevented from the decomposition by gastric acid, a strong acid.

Also, intravenous administration (intravenous injection) enables bolus administration of the drug at high concentration into blood flow. However, it is difficult to deliver the administered drug to the target site at effective concentration, because: the drug in blood is rapidly decomposed or excreted into urine to decrease its blood concentration thereof; it is accumulated in the liver; or it is stayed in the blood flow without targeting. Increase of the amount of the drug to be delivered into the other than target site may causes a serious side effects. Otherwise, frequent administrations of the drug with small amounts are burden both for patients and healthcare professionals. For example, in the former, levodopa, the pharmaceutical preparation for Parkinson's disease, gives low response rate, because its passing amount through blood-brain barrier is too low to give affects. On the other hand, it actually happens that the administration of the increased amount of levodopa causes serious side effect, because levodopa, of which targeting site is brain, is decomposed by the enzyme located at the other sites. As a result, it makes impossible to continue further treatment.

Moreover, such carrier requires is required to have the smallest interaction with the living body being administered as an additional property (biocompatibility), other than that to incorporate higher molecular weight drug, the biopolymer. Additionally, it is required to have another property that it maintains the stable structure while it is delivered to the target site to save the incorporated molecules (the active ingredients) and then it releases them quickly from the carrier.

There is a strong social need for the carrier having such properties and characters, because the carrier has not put into practice until now. Recently, the study using targeting property and biocompatibility of exosome such as natural nanoparticles, or cells, for example, erythrocyte, for DDS have developed. However, encapsulating technique has not been completed so that it is not put to practical use.

It is known that dendrimer forms micelle with a structure composed of hydrophobic moieties inside of them, and reverse micelle with the structure composed of hydrophilic moieties inside of them, under the condition that mixed solvent including organic and aqueous solvents.

As described above, in the past, it has been studies whether the micelle composed of the carbosilane dendrimers carrying hydrophilic groups at the end of their side chains are practically used or not; wherein hydrophilic groups are mentioned for example, such as sugars, amino acids, hydrophilic molecules, and they are held on the micelle outside surfaces. In order to form the micelle, the dendrimer molecule essentially includes the internal hydrophilic group.

However, it is impossible to observe in vivo whether the dendrimers carrying the hydrophilic groups are delivered to the targeted tissue. The reason is that AIE micelle emits lights but weak, depending on their environment.

On the other hand, replacing the hydrophilic group, being held on the molecule, with proteins is considered to be very difficult, because the molecular weight of them are hugely different, and the protein is easily denatured depending on the conditions of the solvent such as its pH, its salt concentration, and the like.

Therefore, there is a strong social need for a complex molecule as a tool for confirming the delivery to the targeted tissue or release amount from the drug at the site, and estimating the amounts thereof. The complex molecule should be composed of carbosilane dendrimers carrying biopolymers having biological targeting ability or biocompatibility with strong fluorescence emission; for example, fluorescent proteins, and it should acquire the ability of the targeted tissue or release amount from the drug at the site, and estimating the amounts thereof by utilizing interaction between two fluorescent molecules.

Means for Solving the Problem

The inventors of the present invention firstly found: mixing the carbosilane dendrimer containing silole and the protein for label, for example, green fluorescent protein, in the aqueous solvent or the mixed solvents composed of the aqueous solvent and the organic solvent by utilizing the reaction between thiols and halogenated alkyls generates aggregatable molecule, and the aggregatable molecule forms the micelle where the protein is outside the aggregatable molecule. Here, the aqueous solvent contains solutes, such as saline, phosphate buffered saline and the like.

Also, the inventors of the present invention further found that the protein carried on the dendrimer induces micelle formation. Moreover, they found that mixing the protein, the carbosilane dendrimer and the model drug gives model drug including micelle. There are mentioned as the example of the model drugs, for example, pigments, antibodies and the like.

Additionally, the inventors of the present invention also found that: the silole containing dendrimer carrying the fluorescent protein emits in saline; and the emission phenomena is caused by fluorescence resonance energy transfer, FRET.

Moreover, they also found that the micelle formed by the silole containing carbosilane dendrimer carrying the fluorescent protein has the inner diameter size of approximately from 50 to 500 nm; and the micelle with the inner diameter size may includes a variety of drugs.

The present invention is completed under the situation as mentioned above, and its purpose is to provide a carbosilane dendrimer enable to incorporate compounds with broad range of molecular weights and the biopolymers, the drugs for DDS using thereof, and the production method thereof.

The present invention comprises the following aspects.

The one aspect of the present invention is aggregatable carrier material for drug delivery system comprising a compound shown in the following formula (I) and a protein and an aggregatable molecule having a targeted sequence presented part, wherein said targeted sequence presented part aggregates in an aqueous solvent to form a micelle having the diameter from 50 to 500 nm, and when said aggregatable molecule aggregates, said aggregated micelles emit fluorescence.

[Chemical formula 1]

$$R^1[(R^2-Si)(-R^3-Y)_3]_2 \qquad (I)$$

Here, $R^1$ is silole group shown in the following formula (II); each of $R^2$ and $R^3$ are a hydrocarbon chain having 1 to 6 carbon atoms which may have the same or a different hydrocarbon chain or a ring; Y is the targeted sequence presented part bound via a halogen group or groups toward sulfur atom in the formula (I).

[Chemical formula 2]

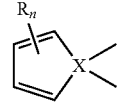

(II)

Here, X is a silicon; R is a phenyl group; and n is 4 in the formula (II). The aggregatable molecule shown in the formula (I) is that shown in the formula (III).

[Chemical formula 3]

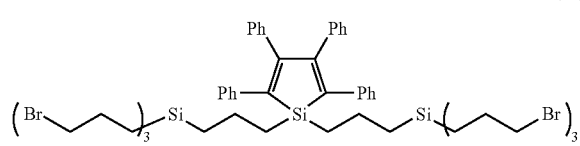

(III)

Also, it is preferable that the aggregatable molecule shown in the formula (I) is selected from the group consisting of the following formulae (IV) to (IX).

[Chemical formula 4]

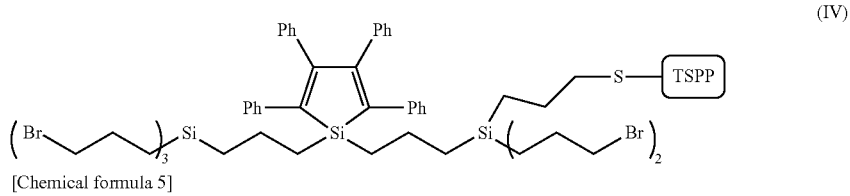

(IV)

[Chemical formula 5]

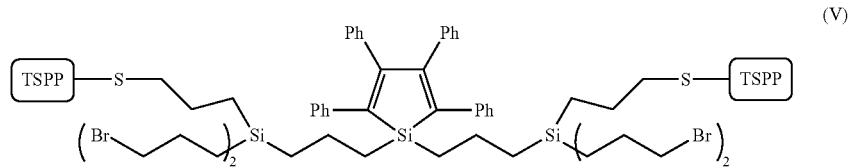

(V)

[Chemical formula 6]

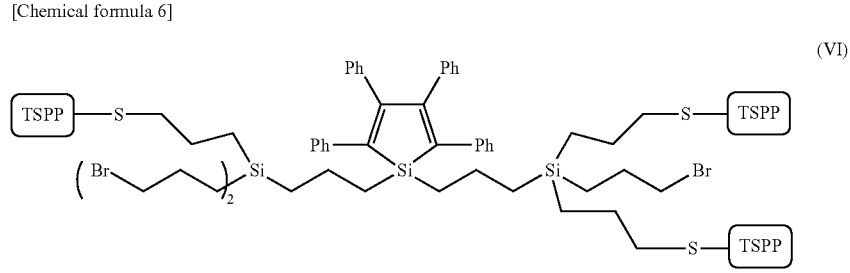

(VI)

[Chemical formula 7]

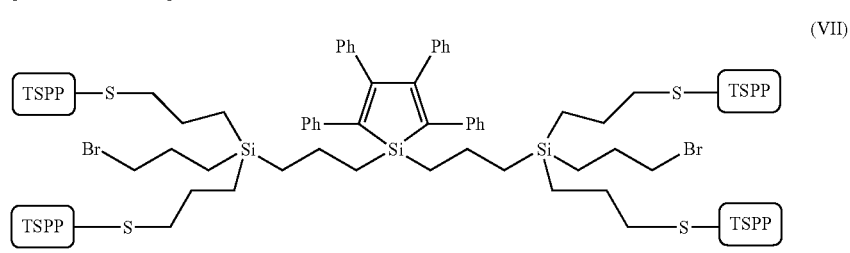

(VII)

[Chemical formula 8]

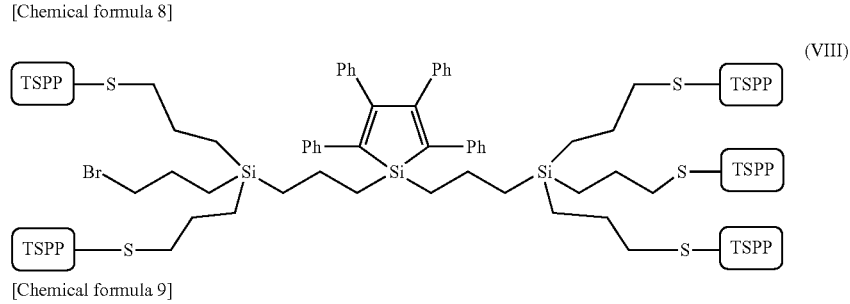

(VIII)

[Chemical formula 9]

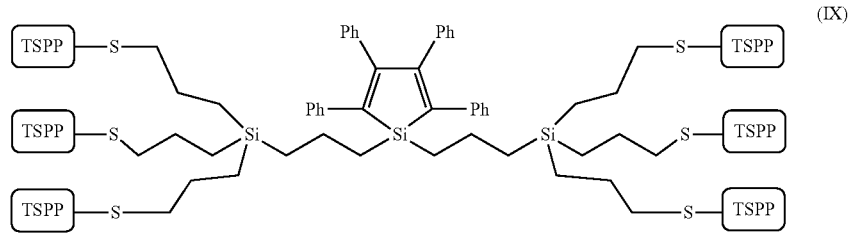

(IX)

TSPP shows a targeted recognition site in the formula. It is preferable that the targeted sequence presented part is composed of a protein having a targeted recognition site. And, it is preferable that the protein is any fluorescent protein selected from the group consisting of a white fluorescent protein, a red fluorescent protein, a yellow fluorescent protein, a blue fluorescent protein and a green fluorescent protein.

Also, the targeted recognition site is preferable any one of functional peptides to deliver the micelle formed by the aggregatable carrier material for drug delivery system to the targeted tissue. The targeted tissue is preferable any tissues selected from the group consisting of the normal tissues having inflammation, the tissues on which undesirable genes are expresses, the cells on which the undesirable genes are expressed, and the tissues composed of tumor cells.

It is preferable that said functional peptide specifically binds to any one of targeted protein selected from the group consisting of a surface antigen, a receptor, a gate, a transporter and a channel to form a conjugate for promoting endocytosis of said conjugate composed of said protein and said functional peptide into a cell.

The another aspect of the present invention is a micelle formed by said aggregatable carrier material for drug delivery system according to claim 1 enables to include any one of molecule selected from the group consisting of a protein having molecular weight of 200,000 or less, a nucleic acid and hydrophobic molecule.

Here, said protein having the molecular weight of 200,000 or less is one of selected from the group consisting of immunoglobulin G, lectins, and peptide hormones.

Advantageous Effect of the Invention

According to the present invention, the aggregatable carrier material for DDS which is needed to produce the carrier for delivering the drugs and the like may be prepared. By using the carrier material, namely the aggregatable molecule, the carrier for the drugs used in DDS, the micelle, may be prepared.

MODE FOR CARRYING OUT THE INVENTION

The present invention is explained in detail below. The present invention is an aggregatable carrier material for drug delivery system comprising an aggregatable molecule having a targeted sequence presented part composed of a compound shown in formula (I) and a protein, wherein said targeted sequence presenting part aggregates in aqueous solvent to form a micelle having the diameter from 50 to 500 nm, and fluorescence is emitted when said aggregatable molecule aggregates.

[Chemical formula 10]

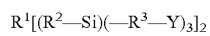

$$R^1[(R^2-Si)(-R^3-Y)_3]_2 \qquad (I)$$

Here, $R^1$ is silole group shown in the following formula (II); each of $R^2$ and $R^3$ are a hydrocarbon chain having 1 to 6 carbon atoms which may have the same or a different hydrocarbon chain or a ring; Y is the targeted sequence presented part bound via a halogen group or groups toward sulfur atom in the formula (I).

[Chemical formula 11]

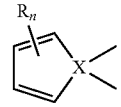

(II)

Here, X is silicon, R is phenyl group and n is 4 in the formula. The carbosilane dendrimer of the present invention (hereinafter, it is sometimes referred to as "silole dendrimer") is further preferably the compound which has the following structure in the following formula (III), since it allows to comprise aggregatable property and targeted sequence part. In the formula, n is an integer from 1 to 3, X shows bromine atom or —S-TSPP. Here, all of X do not become bromine atoms at the same time.

[Chemical formula 12]

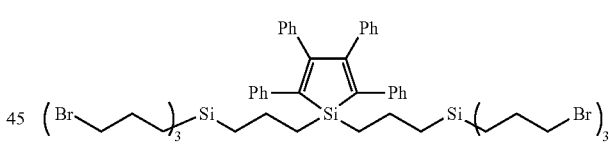

(III)

Figure 1:
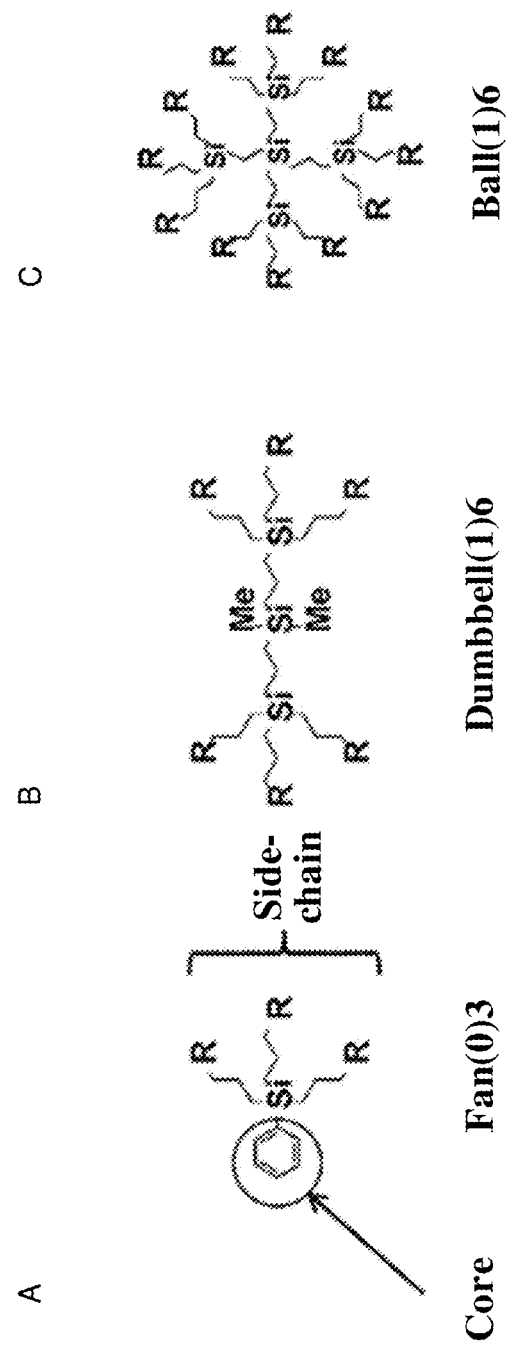
FIG. 1 is a schematic diagram showing basic formula of general carbosilane dendrimers.
Figure 2:
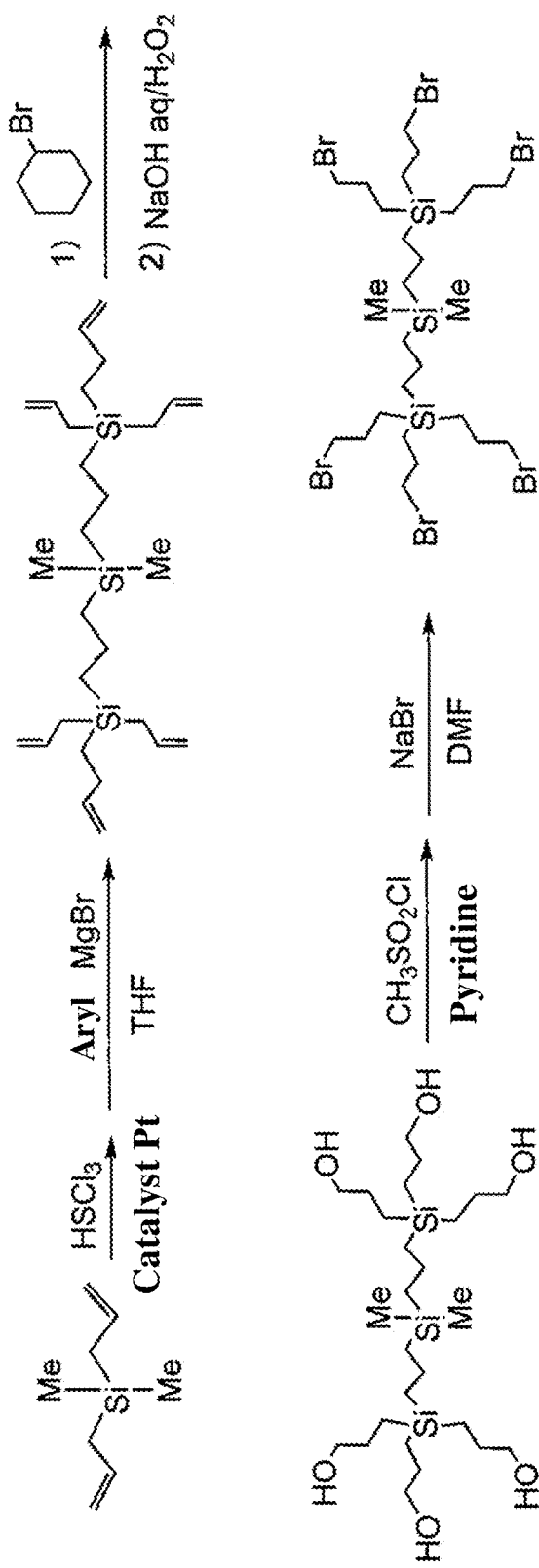
FIG. 2 is the figure showing synthesis scheme of dimethyl dumbbell (1) 6-Br from dimethylsilane.

The structures of typical carbosilane dendrimers are shown in FIG. 1A to 1C. The compound shown in FIG. 1A is called a Fan (0)3 having core, which is surrounded by the circle. The compound in FIG. 1B is called a dumbbell (1)6, wherein two Fan (0)3 shown in FIG. 1A were bounds with a silicon having two methyl group (Me-Si-ME) instead of the core. The compound shown in FIG. 1C is called a ball (1)6. It has a spherical form and is composed of the molecules having the same structure as Fan (0)3 without the core bound to Si of the dumbbell, Me-Si-Me, wherein the methyl groups of the dumbbell are replaced.

The structure of carbosilane dendrimer of the present invention is completely different from those of the conventional carbosilane dendrimers, and one of bromine atom binding to the end of the molecule pertains to form the bond with targeted sequence presented part. Here, the targeted sequence presented part is preferably the protein having the targeted recognition site from the view point that it enables to conduct specific delivery of the drug for DDS composed by the dendrimer.

Also, it is preferable that the protein composing the target sequence has thiol groups, which locates outside the folded protein.

Since the thiol groups react with the halogen atoms contained in the dendrimers to play a role to bind the protein and the dendrimer, the thiol groups located in side of the folded protein may not be involved in forming the bond. Here, the "protein having thiol groups" comprises the protein originally having thiol groups, that having newly introduced thiol groups by using the genetic engineering technique and the like, and that having the thiol groups resulting from the reduction of cysteine in the cysteine including protein.

The positions of the thiol group in the protein are not particularly limited. However, it is sometimes preferable that the thiol groups are positioned in the specific region on the protein. Note that cysteine in the protein including cysteine may be those inserted in the predetermined position by using the gene-engineering technique such as for replacing the existing arbitrary amino acid with cysteine, that for inserting it at the predetermined position and the like. It is easily conducted for the person skilled in the art to introduce cysteine residue at the desirable position in the protein by using the known gene engineering method such as the site-directed mutagenesis and the like.

The protein composing the targeted sequence presented part is preferable to have nature of association (hereinafter, it is sometimes referred to as "associating property"), and it is not limited particularly. However, green fluorescent protein (hereinafter, it is sometimes referred to as collectively "GFP" including the following fluorescent protein which emits fluorescence other than green), and variant thereof are preferably used. Since the carbosilane dendrimer to which the fluorescent protein is bound emits strong fluorescence by the association of the proteins, it makes detection of the association state easy.

As GFPs used in the present invention, there are mentioned, for example, GFP shown as SEQ ID NO: 1 in the sequence listing, GFP shown as SEQ ID NO: 2, BFP shown as SEQ ID NO: 3 in the sequence listing which is blue fluorescent protein, YFP shown as SEQ ID NO:4 in the sequence listing and the like, and also CFP, RFP and other variant GFPs provided from Clontech Laboratories, Inc., and the like. Besides these, the fluorescent protein derived from Discosoma shown as SEQ ID NO: 5 in the sequence listing and the like may be used. However, GFP shown as SEQ ID NO: 1 in the sequence listing is preferably used, because it has strong fluorescence intensity, and also it is easy handled.

Also, such GFPs may be prepared by using known methods, for example, referring to Biochem. Biophys. Acta 1679 (2004) 222-229; Biochem. Biophys. Res. Commun. 330 (2005) 454-460, and the like. Also, GFPs may be used those produced by outsourcing to the protein manufacturing company.

When the dendrimer to form the aggregatable carrier of the present invention is composed of the molecules containing functional groups causing AIE effect such as silole and the like as a framework and associative proteins such as fluorescent protein as the targeted sequence presented part thereby forming the micelle, aggregated siloles also emit fluorescence. As a result, fluorescence resonance energy transfer (FRET: Fluorescence resonance energy transfer) is occurred between the associated fluorescence proteins and gathered siloles, and it makes the fluorescence strong. When the micelle is collapsed, FRET disappears.

Therefore, when the micelle manufactured by using the present invention is used as the carrier for the drug delivery, of which status in vivo may be monitored by using the change of FRET as an index. Moreover, such monitoring enables to trace the location of the carrier and its status possible.

In order to cause FRET between the fluorescent protein and the silole dendrimer, fixed position of the fluorescent protein on the silole dendrimer is important. The person skilled in the art may easily determine the position on the protein onto which binds the dendrimer by a preliminary experiment and the like. When GFP is used as the fluorescent protein, it is preferable to bind a loop region which is contiguous to one region among N-terminal region, C-terminal region, N-terminal region and C-terminal region. It is preferable that the amino acid such as cysteine having thiol group exists in the region.

Here, the binding in the N-terminal region means that the protruding moiety from the core site, such as being composed of 10 amino acids positioned close to the end of N-terminal, is binding to the silole dendrimer. As the same as the case of C-terminal, the protruding moiety from the core site, such as being composed of 10 amino acids positioned close to the end of N-terminal, is binding to the silole dendrimer.

A position of halogen group carried on the silole dendrimer of the invention is not limited particularly. However, it is preferable to located on the side chain of the silole dendrimer. More preferably, it is located at the side chain terminal, which is the most distant position from the silole group, as the formula (III) shows.

As described above, the silole dendrimer used for the method of the present invention is, for example, the compound shown in the above formula (I). And then, the structure of silole dendrimer in the formula (I) is preferably any one of the selected from the group consisting of the following formulae (IV) to (IX).

[Chemical formula 13]

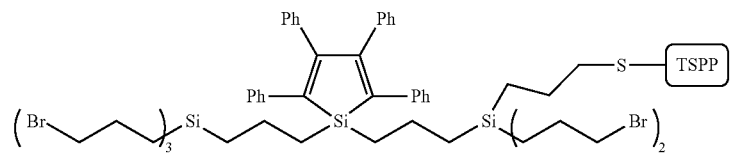

(IV)

[Chemical formula 14]

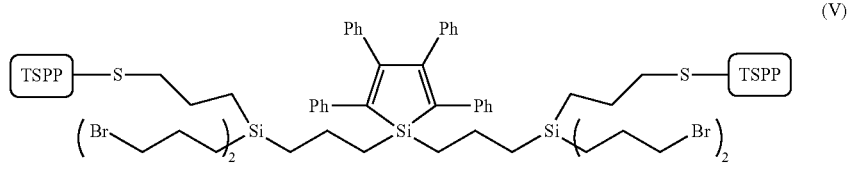
(V)

[Chemical formula 15]

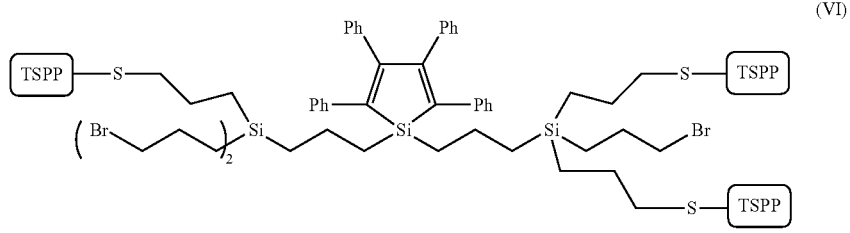
(VI)

[Chemical formula 16]

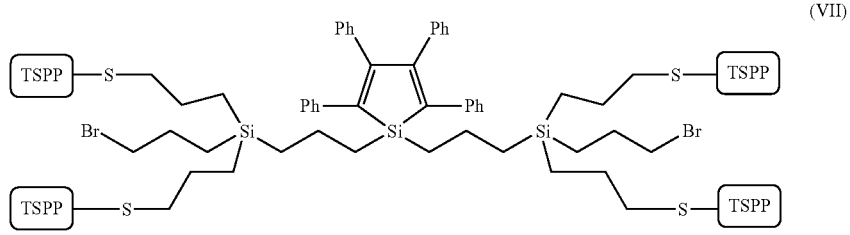
(VII)

[Chemical formula 17]

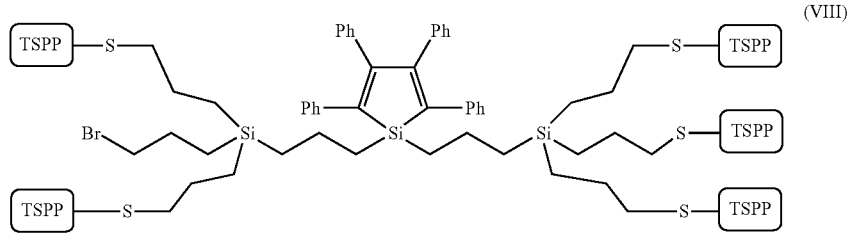
(VIII)

[Chemical formula 18]

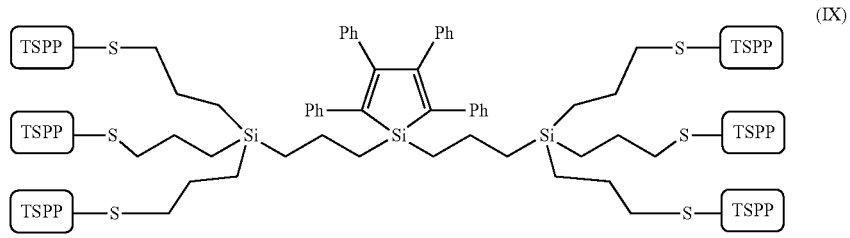
(IX)

As the compound shown in formula (I), for example, the compound shown in formula (III) may be used. The compound may be synthesized, for example, through silole core 2 (1,1-diaryl-2,3,4,5-tetraphenylsilole) from 1,2-diphenylacetylen via the known intermediate 18 as shown in the scheme 1.

Next, the silole core dendrimer 3 is obtained through hydrosilation of 2 with trichlorosilane using $H_2PtCl_6 \cdot 6H_2O$ as a catalyst, and subsequent Grignard reaction by using aryl magnesium bromide. The silole core dendrimer 3 obtained is treated with dichlorohexyl borane and then subjected to hydrolyzation with hydrogen peroxide in alkaline aqueous solution to obtain hexahydroxy derivative 4. Subsequently, the hexahydroxy derivative is subjected to O-mesylation to replace with bromine anion to obtain the compound 5 (Tetrahedron Lett., 2007 48:4365-4368).

[Chemical formula 19]

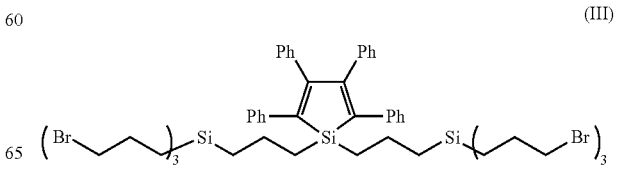
(III)

The protein having the targeted recognition site which composes the targeted sequence presented part is not limited as long as it has association properties. However, the protein is preferably any one of the fluorescent protein selected from the group consisting of the white fluorescent protein, the red fluorescent protein, the yellow fluorescent protein, the blue fluorescent protein and the green fluorescent protein.

It is because that they are easily purchased, and have high intensity fluorescence so that they generate FRET to give strong fluorescence. Here, the blue fluorescent protein includes any of those emits blue or cyan fluorescence.

The aggregatable molecule of the invention is prepared by mixing the protein having thiol group, which is targeted sequence presented part, and the dendrimer compound having halogen group in the side chain shown in formula (III), and then the mixture is incubated to react the thiol group of the protein and the halogen group of the dendrimer compound thereby binding the protein to the dendrimer compound. At this time, it is desirable to previously treat the protein with a reducing agent such as DTT to keep —SH group in non-oxidized condition. Scheme 1 shows the reaction for incorporating one GFP molecule by using the reaction.

Scheme 1

[Chemical formula 20]

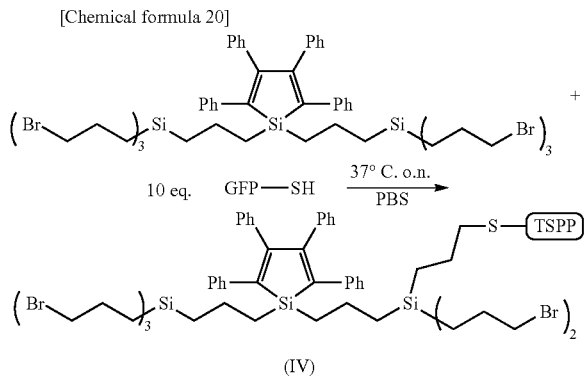

(IV)

For example, the reaction shown in the scheme 1 may be conducted in a proper solvent, for example, an aqueous solvent such as PBS, saline, and the like. The reaction condition in this case is depending on the proteins used. The reaction temperature may be under the denaturation temperature of the protein used, for example, between 0° C. and 50° C., preferably between 30° C. and 45° C., and more preferably about 37° C. When GFP is used, the reactivity may be temperature-dependently improved up to 42° C. Therefore, it is preferable to use GFP for preparing the aggregatable carrier material for DDS.

Also, the reaction time varies depending on the reaction temperature. However, for example, it is from 1 to 24 hours, preferably from 10 to 19 hours, and more preferably about from 15 to 18 hours. It is because that the protein having thiol group used is bound to the silole dendrimer to form the micelle during such reaction time.

That is, as protein-dendrimer complex is formed, the micelle of which outside is composed of the protein, which is the hydrophilic moiety, and of which inside is composed of the core part of dendrimer, which is the hydrophobic moiety. That is, it is considered that the micelle is formed by the driving force generated from the association of the proteins in the binding of the associative protein to the side chain of the dendrimer.

Here, at least one or more proteins are replaced with the halogen atom at the end of side chain to bind to the silole dendrimer. Therefore, the aggregatable carrier material for the drug delivery system obtained through the reaction is obtained as a mixture of the conjugates shown in the chemical formulae (IV) to (IX).

When the protein having thiol group is the fluorescent protein, the mixing ratio of such protein and dendrimer (molar ratio) may be, for example, that the dendrimer is from 1 to 20, when the protein is 1; preferably from 1:5 to 15, and more preferably about from 1:10.

Also, when the reaction is conducted, it is preferable to incorporate an amino acid sequence, which becomes the targeted recognition site, into the protein as the targeted sequence presented part, because it enables to realize the effective delivery in the DDS described later. Such incorporations of the targeted recognition site may be conducted by using Inverse PCR. After the reaction, the unreacted fluorescent protein may be removed by gel filtration and the aggregatable molecules for DDS of the present invention may be obtained.

The incorporation of the targeted recognition site enables specific delivery of the micelle being composed of the aggregatable molecule for DDS of the present invention to the normal tissue having inflammation, the tissue having undesirable gene expressions, the tissue composed of tumor cells and the like. Here, as the example of the normal tissue having inflammation, the tissue having distinctive feature for autoimmune disease and the like may be mentioned. Also, the example such as the tissue having undesirable gene expressions, the tissue having clear relationship between the disease and single base substitution by SNP analysis and the like are mentioned. As the example for the cells having undesirable gene expressions, the cell derived from the tissue on which undesirable genes are expressed as described above may be mentioned. Furthermore, as the example of the tissues composed of the cancer cells, breast cancer tissue, lung cancer tissue, liver cancer tissue, uterine cervical cancer tissue and the like may be mentioned. The amino acid sequences shown in Sequence Nos. 1 to 5 in the sequence listing may be mentioned as the targeted recognition site.

EXAMPLES

The following examples are merely illustrative and do not limit the scope of the invention.

Example 1

Preparation of the Aggregatable Molecules and Micelles for DDS

In the example, the following GFP was used as the protein and the silole dendrimer was used as a dendrimer.

(1) Preparation of the Aggregatable Molecule for DDS

In the example, the compound having the following chemical formula (X) (hereinafter, it is sometimes referred to as "dimethyl dumbbell (1) 6-Br") as the dendrimer having halogen group, and GFP (green fluorescent protein) (sequence No. 1) was used as the protein having thiol group.

[Chemical formula 21]

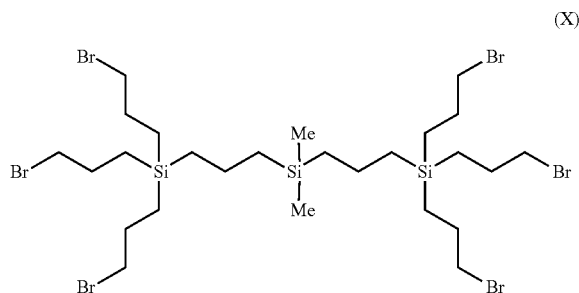

(X)

The GFP (SEQ ID NO: 1 in the sequence listing) used here was prepared according to the method that had already been reported by the inventor et al. (see Biochim. Biophys. Acta 1679 (2004) 222-229; Biochem. Biophys. Res. Commun. 330 (2005) 454-460). The amino acid sequence of GFP shown in the SEQ ID NO: 1 has replaced the amino acid at the position 251 in the C terminal region with cysteine, and originally presented cysteine at the position 60 was replaced with serine.

At first, DTT was added to GFP solution of 20 μM concentration (phosphate buffered saline, hereinafter, it is abbreviated as "PBS") at 1 mM as a final concentration, and the GFP solution was treated for 10 minutes at room temperature to reduce cysteines on the surface of GFP. Ten μL of 200 μM of silole dendrimer shown the formula (III) solution (in DMSO solution) was added to 400 to 450 μt of 20 μM GFP solution (in PBS) to have the final concentration of 10-fold molar equivalent, and then mixed with vortex mixer.

After vortex, the solution was stood at 37° C. for overnight incubation to bind GFP and the silole dendrimer, and subsequently to form the micelles. The incubation time for this experiment was about 16 to 18 hours. The properties of the micelle particles in the solution were measured by using dynamic light scattering method (DLS; Dynamic light scattering). The result was shown in Table 1.

TABLE 1

Average particle diameters of raw materials and products in PBS measured 5 times at 25° C. [nm]

| | Zeta Average | Particle diameter peak by scattering intensity | Particle diameter peak by number |
|---|---|---|---|
| 20 μM GFP only | 860.7 | 838.8 | 4.682 |
| 50 μM Silole only | 894.5 | 664.6 | 649.3 |
| 20 μM GFP-Silole only | 210.3 | 256.8 | 147.7 |

Figure 3:
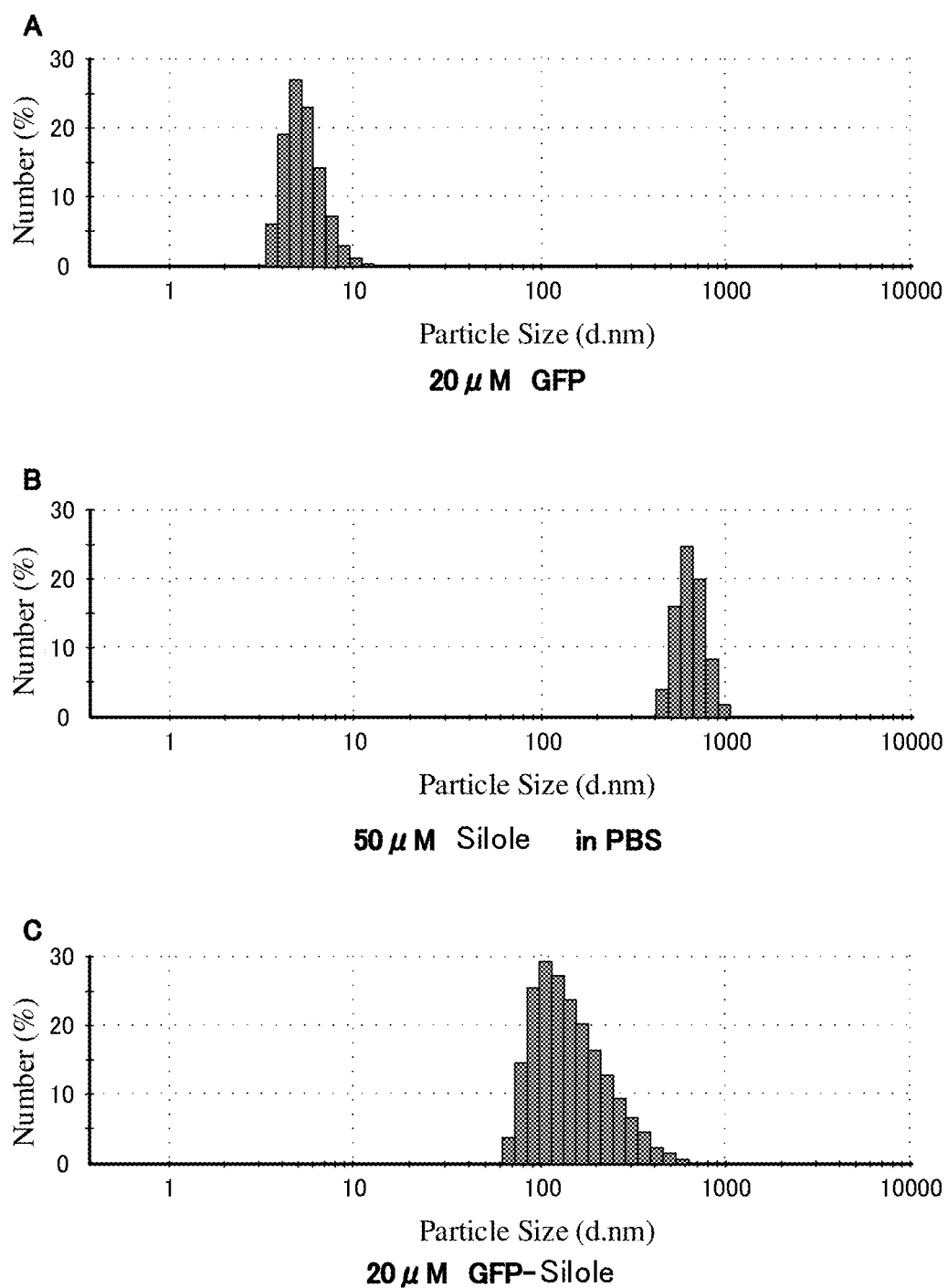
FIG. 3 is the graph showing particle size distribution of prepared micelles.

Also, the particle size in the reaction mixture was measured at 25° C. by using ZETASIZER NANO-S(manufactured by Malvern Instrument Ltd.) with a laser beam wavelength of 532 nm. The result was shown in FIG. 3. FIG. 3A shows the result that GFP only was incubated and the particle sizes of the obtained products were measured. FIG. 3B shows the result that only the silole dendrimer was incubated and the particle size of the obtained product was measured. FIG. 3C shows the result that GFP and the silole dendrimer shown in formula (III) were mixed and incubated, and the particle sizes of the obtained products were measured. The horizontal axis shows the particle sizes of the obtained products, and the vertical axis shows the percentage of the whole products with the sizes shown on the horizontal axis.

When GFP and the silole dendrimer were incubated (GFP-Silole only), the particle size of the micelle obtained was about 150 nm. In contrast, the particle size observed when GFP only was incubated was about 4 nm, and the particle size observed when silole dendrimer only was incubated was about 650 nm. It was considered that the reason why the large size particles were observed is caused by the aggregation among the silole dendrimers in the incubation of silole dendrimer only to form large aggregates.

Figure 4:
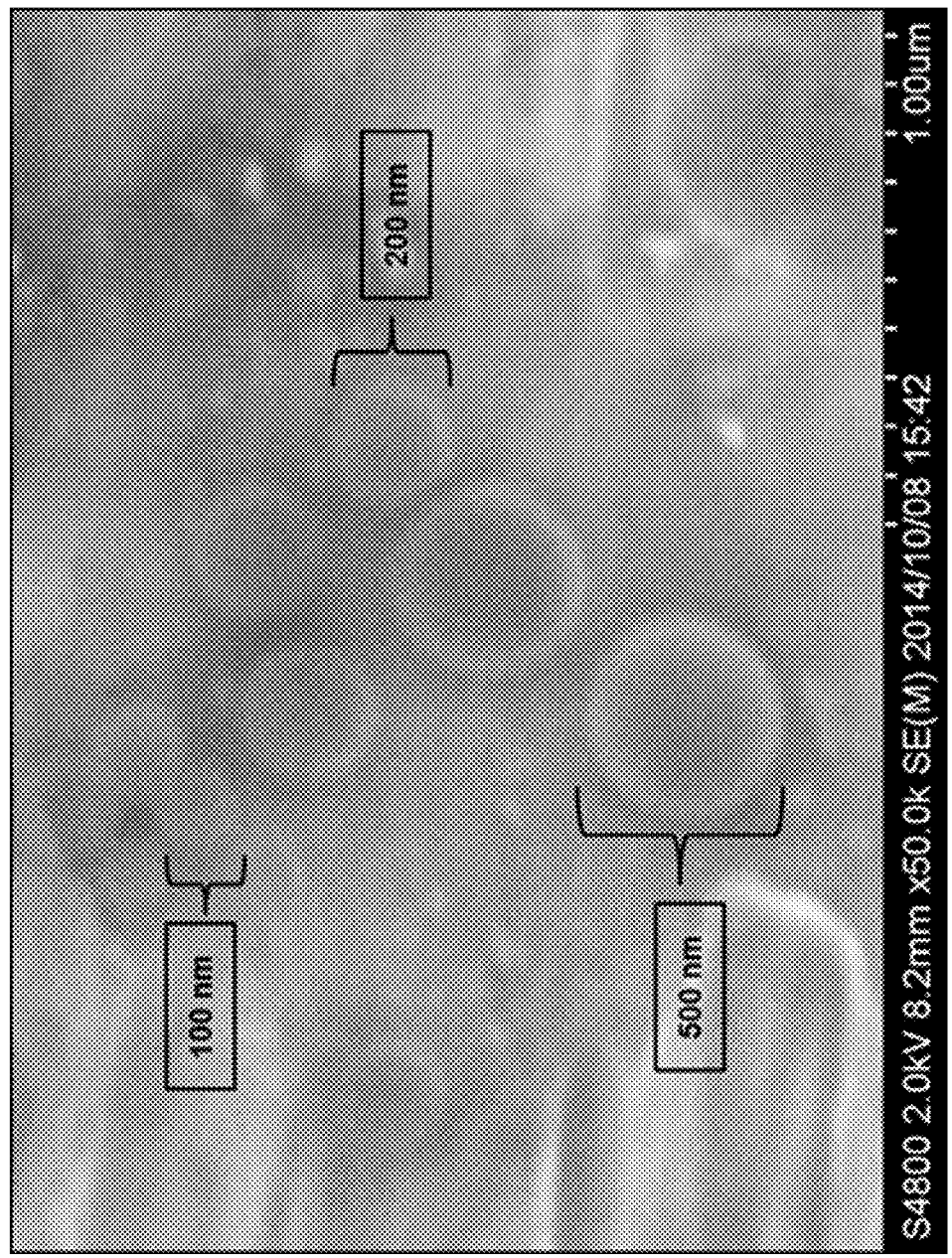
FIG. 4 is a typical electron micrograph of the prepared micelle observed by using a scanning electron microscope.

Next, according to the observation of the obtained micelle particles by using scanning electron microscope (SEM; Scanning Electron Microscope), a large number of particles having the particle size of about from 100 to 500 nm and a small number of those of about 500 nm were confirmed (see FIG. 4).

From these results, it was clearly demonstrated that the micelle formed by using the aggregatable carrier for DDS of the present invention has the particle size distribution range between about 100 and 500 nm, and there were many particles having the particle size range between about 100 and 200 nm. Also, the electron micrograph by using SEM demonstrated that these particles have spherical micelle structures.

The silole dendrimers used in the example have the emission property, when the hydrophobic core parts of the silole were aggregates, AIE effects; and then, it was confirmed that the dendrimers emit, when they form the micelle structures. Therefore, we examined whether fluorescence resonance energy transfer (FRET: Fluorescence resonance energy transfer) between the silole and GFP occurs or not in the micelles composed of GFP-silole dendrimers to which GFP binds to the silole dendrimer.

Figure 5:
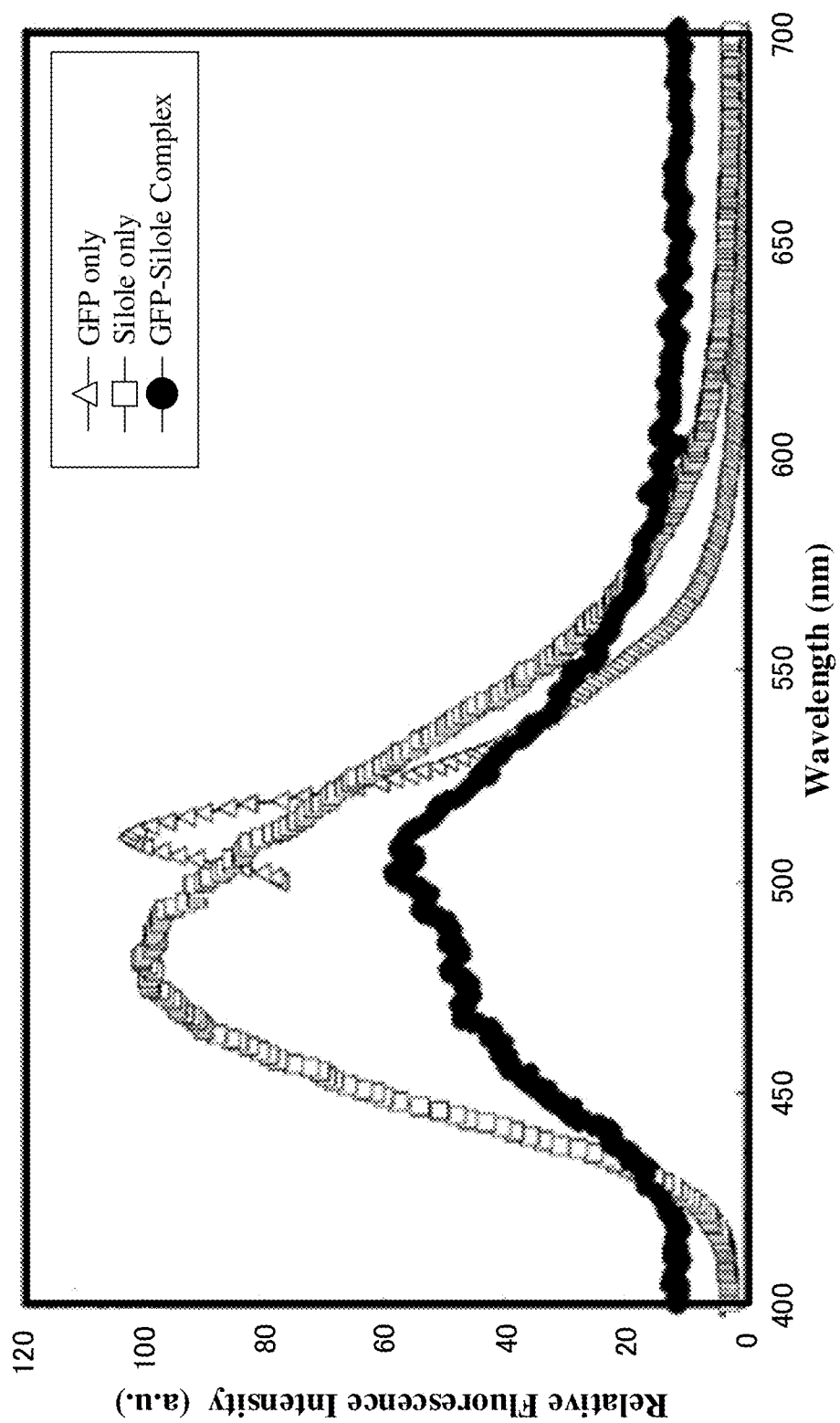
FIG. 5 is the graph showing the emission property of the products obtained by incubating the complex of GFP and silole dendrimer shown in formula (III) (hereinafter, it is referred to as "GFP-silole dendrimer complex"), GFP only, or silole dendrimer only shown in formula (III).

Unreacted fluorescent proteins and dendrimers, free molecules, were removed from the reaction mixture, we conducted the emission property experiment (see FIG. 5). In order to examine the emission properties, the incubated products containing the silole dendrimer only was excited at a wavelength of 360 nm (white square), these containing GFP only was excited at the wavelength of 488 nm (white triangle), these containing both of GFP and the silole dendrimer was excited at the wavelength of 360 nm (black circle). The micelle being composed of silole-GFP conjugates, which is the products obtained by incubating GFP and silole dendrimer in formula (X), showed the emission caused by FRET around 510 nm.

As shown in FIG. 5, the silole dendrimer showed the emission peak around 480 nm. Also, the conjugate of GFP and silole dendrimer did not show a sharp emission peak, but it has the highest value around 510 nm. In contrast, GFP showed the sharp emission peak around 510 nm, and it was considered to be due to FRET from the silole dendrimer to GFP. When the micelles were collapsed, the emission from GFP considered to be caused by FRET, was also disappeared.

That is, when the micelles were prepared by using the molecules, which are composed of the dendrimer having AIE effect and the associative protein such as fluorescent protein, the GFP-silole conjugates, they give FRET between the dendrimers and GFP, and collapsed micelle lost FRET.

From the above, when the micelle of the present invention was used as the aggregatable carrier for DDS, the tissues or organs, to which the micelle was delivered may be confirmed. Also, the fluorescence from the fluorescent protein may be traced even after the micelle delivered to the targeted tissue or organ collapses. Thereby, the intracellular environment and the like may be detected by using the delivered fluorescent protein into the cell.

(3) Experiment for Inclusion of Drugs and the Like into the Micelle Composed of GFP-Silole Dendrimer Complex Next, it was confirmed whether the micelle of the present invention is used for drug inclusion. In the experiment, DiI (1,1'-dioctadecyl-3,3,3',3'-tetramethyl indocarbocyanine perchlorate, Promokine PK-CA707-60010, manufactured by PromoCell GmbH), Oil orange SS (manufactured by Tokyo Chemical Industry, product No:T0553), goat anti mouse IgG (manufactured by Abcam plc, product No. ab6708)-Alexa610 (manufactured by Molecular Probes, product No.: A30050) and WGA (Wheat Germ Agglutinin: wheat germ agglutinin, manufactured by Molecular Probes) (WGA-Alexa Fluoro (registered trade mark) 594 conjugate, product No.: W11262) were used as model drugs.

Ten μt of 200 μM of the silole dendrimer (in DMSO solvent) shown in the formula (III) was added to 20 μM of GFP, of which cysteine was reduced, to have final concentration of 10-fold molar equivalent, and any one of followings was added and mixed with vortex mixer, and incubated overnight at 37° C. (about 16 to 18 hours): DiI (final concentration; 1 μM, fluorescent dye), Oil orange SS (final concentration; 20 μM, fluorescent dye), goat anti mouse IgG-Alexa 610 (final concentration; 0.1 μM) and WGA (final concentration; 2 μM).

It was measured whether the micelles including each drug are formed in the sample to which each model drug is added; and if the micelles including the drug are formed, their particle size were measured by using the dynamic light scattering method. The results were shown in Table 2. Here, DiI, Oil orange SS, and goat anti mouse IgG-Alexa 610 were used as drug models.

Figure 6:
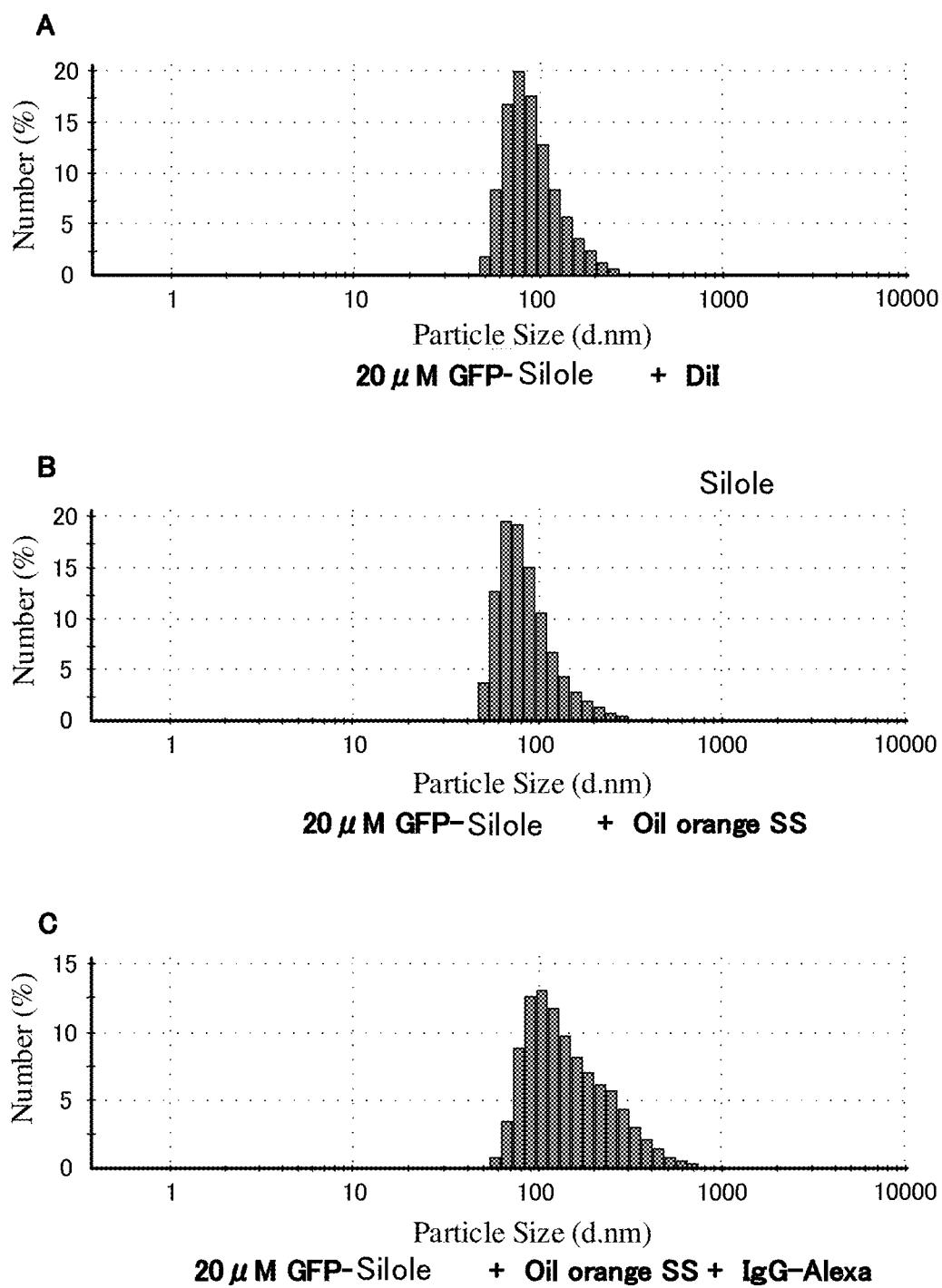
FIG. 6 is the graph showing the particle size distribution of the micelle prepared in the presence of the model drug.

FIG. 6A to C show the particle size distributions, when the model drugs were used. FIG. 6A shows the distributions in the presence of DiI; FIG. 6B shows these in the presence of Oil orange SS; and FIG. 6C shows these in the presence of goat anti mouse IgG-Alexa 610 respectively, when the micelles were prepared with these model drugs. The horizontal axis shows the particle size of the micelle, and the vertical axis shows the percentage of the micelles having each size shown on the horizontal axis against the whole micelle numbers. When DiI was added, the micelle size was about 95 nm; also when Oil orange SS was added, it is about 95 nm; and when IgG-Alexa 610 was added, it was about 180 nm.

TABLE 2

Average particle diameter of raw material and product in PBS measured 5 times at 25° C. (nm)

| | Zeta Average | Particle diameter peak by scattering intensity | Particle diameter peak by number |
|---|---|---|---|
| 20 μM GFP-Silole only | 210.3 | 256.8 | 147.7 |
| 20 μM GFP-Silole + DiI | 137.3 | 159.6 | 95.27 |
| 20 μM GFP-Silole + Oil orange SS | 147.6 | 177.2 | 94.77 |
| 20 μM GFP-Silole + Antibody-Alexa 610 | 277.7 | 324.3 | 179.7 |

Figure 7:
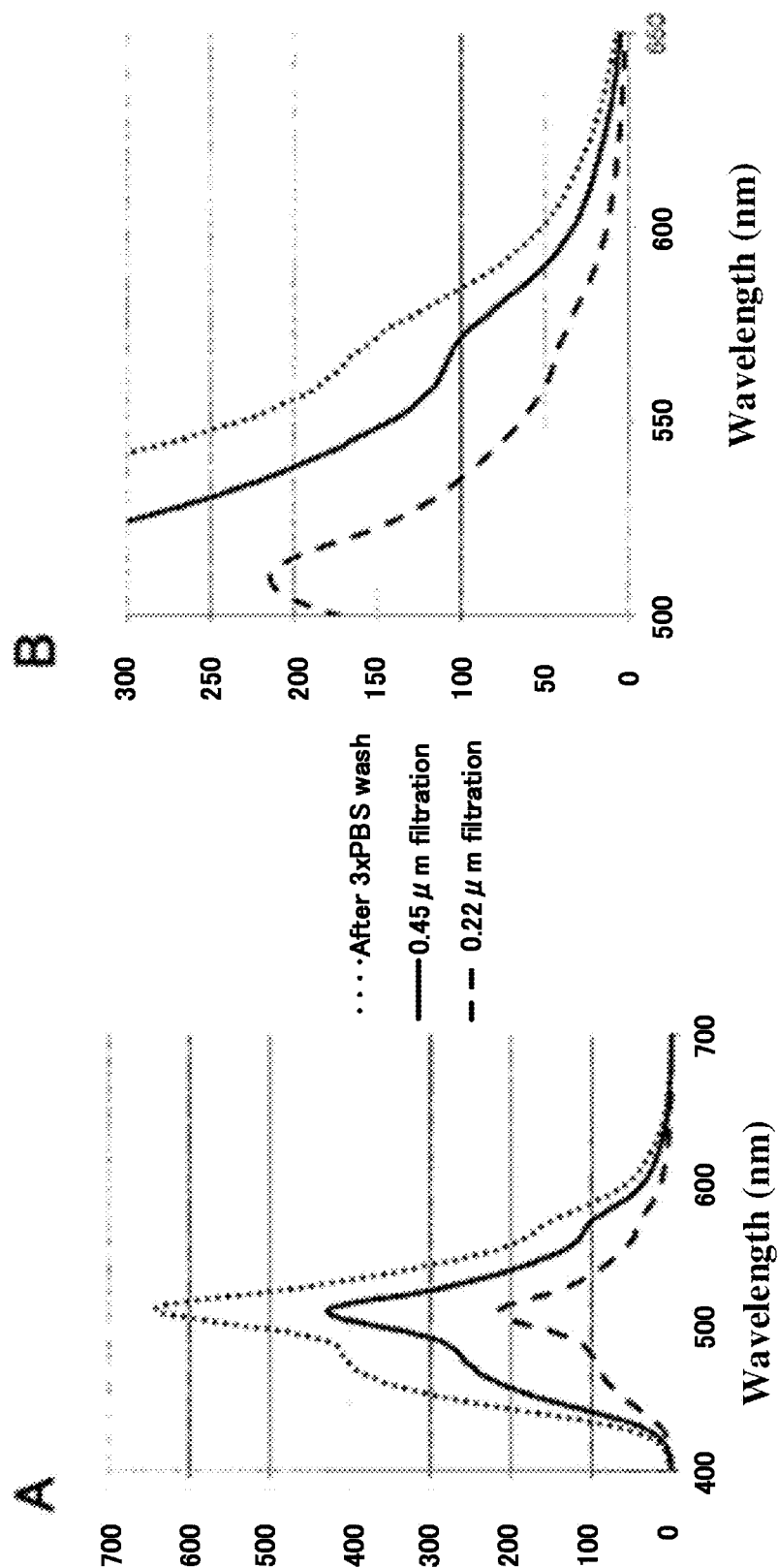
FIG. 7 is the graph showing the emission property, when the micelle consisting of GFP-silole dendrimer complex and it includes DiI. The micelle was excited at 360 nm.

FIG. 7 shows the examination result for the emission properties of the micelles including DiI, the fluorescent dye. FIG. 7B shows enlarged drawing of the spectrum in FIG. 7A, around 500 nm. The horizontal axis shows wavelength (nm), and the vertical axis shows relative fluorescent intensity (a.u.). At first, the micelles including DiI were prepared, and following test samples were prepared for measuring their fluorescence: the micelles washed 3 times with PBS; the filtered reaction mixture through a filter having a pore size of 0.45 μm to remove free dye; and the filtered reaction mixture through the filter having the pore size of 0.22 μm instead of the filter having the pore size of 0.45 to remove free dye.

As shown in both FIGS. 7A and 7B, shoulder peaks were observed around the wavelength of 480 nm, when the samples were excited at the wavelength of 360 nm. It was considered that these peaks appeared the emission from the silole. It was considered that the peak around 510 nm appeared FRET from the silole to GFP; and the peak around 570 nm appeared FRET from the silole to DiI. From these results, it was confirmed that DiI was included in the micelle.

Figure 8:
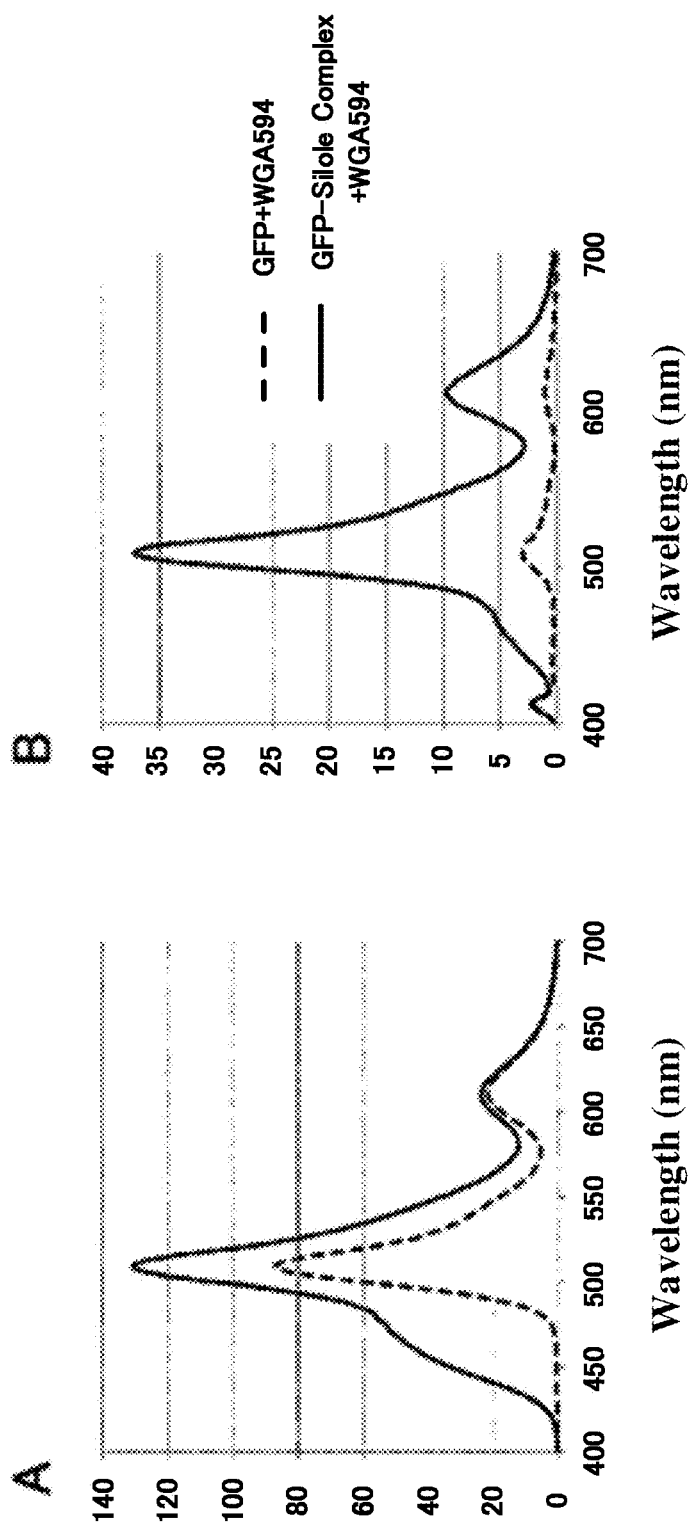
FIG. 8 is the graph showing the emission property, when the micelle consisting of GFP-silole dendrimer complex and it includes WGA labeled with Alexa 594. The micelle was excited at 360 nm.

Next, the emission properties of the micelles including WGA labeled with Alexa 584 was examined (see FIGS. 8A and B). FIG. 8A shows the measurement results of the reaction mixture in situ, when Alexa 594 labeled WGA was added. Also, FIG. 8B shows the results after removal of the unincorporated stuffs into the micelles such as the unreacted proteins, Alexa labeled WGA, the silole dendrimer, or GFP by using the ultrafiltration spin column (manufactured by Millipore). In FIG. 8, the solid line shows the emission property of the products obtained by mixing treatment of GFP-silole dendrimer complex and WGA; and the broken line shows that of the products obtained by mixing treatment of GFP and WGA.

In the figure, the solid line shows the measurement result for the micelle composed of GFP-silole dendrimer complex including Alexa 594 labeled WGA; and the broken line show the measurement result for that including the mixture of GFP and Alexa 594 labeled WGA respectively (Excitation wavelength is 360 nm in each case).

FIG. 8 shows the measurement result for the reaction mixture without the ultrafiltration spin column treatment in situ. In FIG. 8A, the emission from the silole dendrimer, GFP and WGA were detected around 480 nm, 510 nm and 610 nm respectively. In contrast, as shown in FIG. 8B, the sample with the ultrafiltration spin column treatment did not show the emission from the free silole dendrimer, GFP and WGA, because they were removed (the dotted line). From the above, it was confirmed that Alexa 594 labeled WGA was included the prepared micelle.

Example 2

Preparation of the Fluorescent Protein Which Binds the Target Peptide Sequence

The target peptide sequence binding fluorescent protein was prepared as follows. The protein bound to the micelle of the present invention at the C terminal, and it bound to the target peptide, which binds the receptor expressed on the surface of a cancer cell, at N terminal.

(1) Inverse PCR (1-1) Selection of the Peptide Sequence

The peptide sequence of the selected target peptide was shown in the following Table 3. MCF-7 is a human breast adenocarcinoma-derived cell.

TABLE 3

| Cell Type | Peptide Sequence | SEQ ID NO: |
|---|---|---|
| MCF-7 | DMPGTVLP | 6 |

(1-2) Preparation of Primers

Primers for conducting inverse PCR of the peptide sequence shown in Table 3 were written in the following Table 4. These primers were designed so as that elongation reaction initiates between DM and PGTVLP of the peptide sequence.

TABLE 4

| Peptide Sequence | Primer | SEQ ID NO: |
|---|---|---|
| DMPGTVLP | F: CCTGGTACTGTTCTTCCTGGTGGTATGAGTAAAGGAGAAGAACTT | 7 |
| | R: CATATCGCGACCCATTTGCTGTCCACC | 8 |

(1-3) Preparation of the Template Plasmid for Inverse PCR

A template plasmid for inverse PCR was prepared by the method described in the following paper.

"Protease-sensitive signaling by chemically engineered intramolecular fluorescent resonance energy transfer mutants of green fluorescent protein." Miho Suzuki, et al. Biochimica et Biophysica Acta (BBA)—Gene Structure and Expression Volume 1679, Issue 3, 17 Sep. 2004, Pages 222-229

(1-3-1) Plasmid Construction for GFPuv5 Mutant

GFPuv5 was prepared from the pGFPgcn4 by a synonymous mutation for gene manipulation by using inverse PCR with I167T mutation and forward primer, 5'CATTGAA-GATGGCTCCGTTCAA (Sequence No. SEQ ID NO: 9) and reverse primer, 5'CATTGAAGATGGCTCCGTTCAA (Sequence No. SEQ ID NO: 10), and the subsequent cyclization treatment. The construct obtained in this way was named pGFPgcn5.

After that, cDNA of GFPuv5 was cloned into pET21a (manufactured by Novaben Inc.) to express the protein, and then the protein was purified and named GFPuv5tag. The code region was amplified using the primers

```
                                         (SEQ ID NO: 11)
5'CTCGACCAT[ATGGCTAGCATGACTGGTGGACAGCAAATGGGT]
CGCATGAGTAAAGGAGAAGAACTTTTCA
and
                                         (SEQ ID NO: 12)
5'TGACGTGAATTCATTA[GTGATGGTGATGGTGATG]TTTGTAGA
GCTCATCCATGC.
```

In SEQ ID NO: 11, an adhesive tag adhering to the epitope tag composed of 11 amino acids from the terminal for 10 proteins of T7 gene toward N terminal of GFPuv5 series was marked as [ ]. SEQ ID NO:12 provides His tag to C terminal of GFPuv5 series, and His tag in the sequence was shown as [ ].

These were inserted into pET21a, and then it was digested with both of NdeI and EcoRI. The pGFPgcn plasmid was used for gene manipulation and the pET21a plasmid was used for protein expression under the control of the T7 promoter. The nucleotide sequences of the gene of GFPuv5 and the mutants thereof were confirmed by DNA sequencing (ABI PRISM 3100, manufactured by Genetic Analyzer).

Three more synonymous mutations were found during the experiment: agt to agc at Ser at 30, cat to cac at His 78, and caa to cag at Gln 183.

The experiment was continued including these mutations, because these mutations were not harmful for the fluorescent proteins. The fluorescent intensity of the purified GFPuv5tag was about 1.9 times higher than that of GFPuv4tag. After that, either of the cysteine residues at position 48 or position 70 was replaced with randomized amino acid by inverse PCR using pGFPgcn5.

Both oligonucleotides 5' CTTAAATTTATTNNKACTG-GAAAAC (Sequence No. SEQ ID NO: 13) and 5'GGTAAGTTTTCCGTATGTTG (Sequence No. SEQ ID NO:14) were used for mutation of cysteine 48, and both of 5'GTGTTCAANNKTTTTCCCGTTATCCG (Sequence No. SEQ ID NO: 15) and 5'CAT-ACGTCAGAGTAGTGACAAG (Sequence No. SEQ ID NO: 16) were used for the mutation of cysteine 70. Culture of *Escherichia coli*. BL21 (DE3) was transformed with the obtained plasmids and screened by using daylight excitation for those having strong fluorescence, and selected on an agar medium. Several mutants emitting strong florescence were obtained at position 48 (replaced with one of Ala, Asp, Glu, Gly, Ile, Leu, Asn, Pro, Ser, Thr, Val, and Tyr). However, the C70V cysteine mutant gave only proper fluorescence at position 70.

In order to produce double cysteine mutations GFPuv5 having strong fluorescent intensity, the plasmid having the single mutation was digested with both of NcoI and EcoRI and ligated to each region again. Selection was conducted by using the single mutants. The UVSCO tag (C48S/C70V) showed the highest fluorescence intensity among all the recombinants Next, cysteines were introduced at both positions 6 and 229 by inverse PCR, respectively. The plasmid having C48S mutation and a set of the following primers were used for introducing respective mutation.

```
For Glu replacement:
                                         (SEQ ID NO: 17)
5'TGTCTTTTCACTGGAGTTGTCCC
and
                                         (SEQ ID NO: 18)
5'TTCTCCTTTACTCATTTTTC For Ile replacement:
                                         (SEQ ID NO: 19)
5'TGCACACATGGCATGGATGAGCTC
and
                                         (SEQ ID NO: 20)
5'CCCAGCAGCAGTTACAAACTC
```

Three protease tags having trypsin target sequence (Glu-Gly-Arg) have various spacer sequence, which were no spacer, Thr spacer or Gly-Thy spacer, and necessary cysteine was replaced between His-231 and Asp-231. These constructs were obtained by using puvC48Stag, the obtained plasmid (a template), and the following primer.

```
                         (for no spacer: SEQ ID NO: 21)
5'CAGCGCCGTTGTGAGCTCTACAAATAATGAATT (for Thr spacer: SEQ ID NO: 22)
5'ACATGTGAGCTCTACAAATAA
and
```

```
            (for Gly-Thr spacer: SEQ ID NO: 23)
5'GGAACATGTGAGCTCTACAAA (Reverse primer)
                     (for no spacer: SEQ ID NO: 24)
5'TGTAATCCCAGCAGCAGTTAC (for T and GT spacers: SEQ ID NO: 25)
5'ACGGCCCTGTGTAATCCC
```

The obtained plasmids were named pUV5trypS0tag, pUV5-trypS1tag and pUV5trypS2tag respectively. Refer to Table 1 for details.

(1-3-2) Purification of GFPuv5Tag Mutant

E. coli BL 21 (DE3) was transfected with all of the plasmids. 12 mL of E. coli at the stationary phase after overnight culture was seeded in 38 ml of LB medium supplemented with 50 μg/ml ampicillin and 0.5 mM IPTG, and incubated at 37° C. for 8 hours. The cells were collected by centrifugation at 2,500×g for 20 minutes and resuspended in 10 mL of PBS. The pellet of the cells was lysed in 10 ml of lysis buffer (pH 8.0) containing 50 mM Tris and 8M urea at room temperature for 15 minutes, and then vortexed. The lysed cells were centrifuged at 1,200×g for 15 minutes, and the supernatant was taken to mix with Ni2+NTA resins (manufactured by Qiagen Co. Ltd.) which were suspended in PBS. After sequentially washing the resins with PBS and 20 mM imidazole, the bound GFPuv5tag mutant was eluted with 250 mM imidazole solution.

In order to exchange the buffer, the eluate was applied to PD-10 gel electrophoresis filtration column (manufactured by Amersham Bioscience Co. Ltd.), which was equilibrated with 10-fold diluted PBS. The eluted GFPuv5tag mutant protein was collected, and the concentrations thereof were determined by using Coomassie protein assay reagent (manufactured by Pierce Co.). Purified GFPuv tag mutants were analyzed by 15% SDS-PAGE.

Nucleic acid sequence of the template plasmid for inverse PCR was shown as Sequence No. SEQ ID NO:26.

(1-4) Conditions for PCR

A reaction mixture shown in the following Table 5 was prepared, and inverse PCR was conducted under the condition shown in the following Table 6.

TABLE 5

| Composition | Amount (μL) |
|---|---|
| Template(plasmid–> pET21a(+)NSS25 | 5 |
| KOD Dash Buffer (manufactured by TOYOBO Co., LTD.) | 5 |
| 2 mM dNTP (manufactured by TOYOBO Co., LTD.) | 5 |
| F primer (2.5 pmol) | 10 |
| R primer (2.5 pmol) | 10 |
| KOD Dash (2.5 U/μl) (manufactured by TOYOBO Co., LTD.) | 0.5 |
| Sterilized distilled water | 14.5 |
| Total | 50 |

TABLE 6

| Temperature (° C.) | Reaction time (min) | Cycle |
|---|---|---|
| 95 | 3 | — |
| 98 | 0.1 | 5 |
| 65 | 2 | |
| 70 | 4 | |
| 98 | 0.1 | — |

TABLE 6-continued

| Temperature (° C.) | Reaction time (min) | Cycle |
|---|---|---|
| 74 | 2 | 25 |
| 70 | 4 | |
| 70 | 7 | |
| 4 | — | — |

(1-5) Confirmation by Gel Electrophoresis

Figure 9:
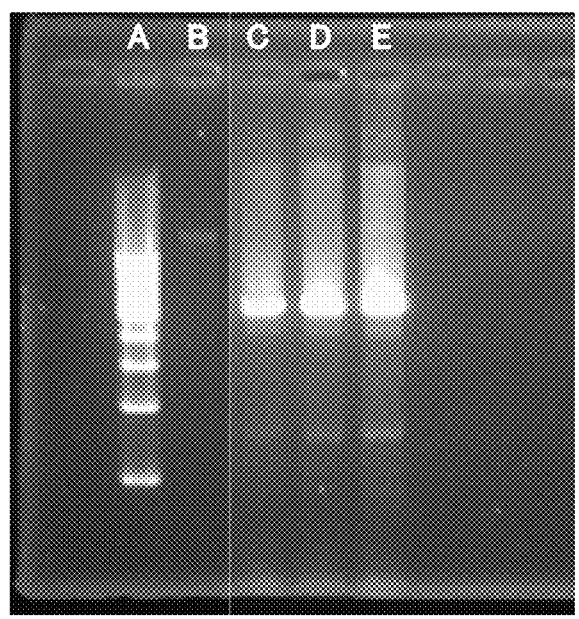
FIG. 9 is an electrophoresis gel image of inverse PCR product after inverse PCR at different annealing temperatures.

A portion of the PCR solution was taken, and subjected to gel electrophoresis with 0.8% PAGE at voltage 100V for 30 minutes of applied voltage time to confirm the amplified peptides in each sample. The result of the electrophoresis was shown in FIG. 9

(2) Removal of Independent A Sequence and Purification of PCR Products

The reaction mixture shown in the following Table 7 was prepared and reacted at 120° C. for 30 minutes to remove the independent A sequence which was produced by the PCR. After that, the PCR products were purified by using QIAquick (a registered trademark), PCR Purification Kit (manufactured by QIAGEN) according to the instruction attached to the kit.

TABLE 7

| Composition | Amount (μL) |
|---|---|
| Inverse PCR products | 50 |
| 10 x NE Buffer 2.1 (manufactured by New England Biolabs Inc.) | 1 |
| 10 mg/ml BSA (manufactured by New England Biolabs Inc.) | 2 |
| 2 mM d NTP | 8.3 |
| T4 DNA polymerase (3000 unit/μl) (manufactured by New England Biolabs Inc.) | 0.5 |
| Total | 60 |

(3) Ligation Reaction

Subsequently, the reaction mixture shown in the following Table 8 was prepared and reacted at 160° C. for more than 3 hours to prepare a circular plasmid for transformation of E. coli DH5α described later.

TABLE 8

| Composition | Amount (μL) |
|---|---|
| Purified PCR products | 8 |
| 10 x T4 ligase B (manufactured by New England Biolabs Inc.) | 1 |
| T4 DNA polynucleotide kinase (400000 unit/μl) (manufactured by New England Biolabs Inc.) | 0.5 |
| T4 DNA ligase (10000 unit/μl)(manufactured by New England Biolabs Inc.) | 0.5 |
| Total | 10 |

(4) Transformation of E. coli DH5α

10 μL of E. coli DH5αa competent cells (manufactured by BioDynamics Laboratory) was thawed on ice immediately before use, and prepared a competent cell solution. One μL of the ligation reaction solution was added to the competent cell solution, and left on ice for 30 minutes. After that, the solution was incubated at 42° C. for 30 seconds and then cooled on ice for 2 minutes. 90 μL of SOC medium (manufactured by TOYOBO Co., LTD.) was added to the solution, and reacted on a shaker at 37° C. for 1 hour. Thereafter, it was seeded on LB selection medium supplemented with ampicillin (manufactured by TOYOBO Co., LTD.), and incubated for overnight at 37° C.
(5) Colony PCR
Colonies obtained from the transformation were subjected to Colony PCR to confirm the predicted inserts.
(5-1) Preparation of the Reaction Mixture for PCR
The reaction mixture for colony PCR shown in the following Table 9 was prepared.

TABLE 9

| Composition | Amount (μL) |
|---|---|
| KOD Dash Buffer (manufactured by TOYOBO Co., LTD.) | 2 |
| 2 mM dNTP | 2 |
| Double His primer (2.5 pmol) | 4 |
| pET primer | 4 |
| KOD Dash (2.5 U/μl) (manufactured by TOYOBO Co., LTD.) | 0.2 |
| Sterilized distilled water | 7.8 |
| Total | 20 |

The reaction mixture for colony PCR was poured into a PCR tube, E. coli grown on the LB medium supplemented with ampicillin was collected and added to the tube. PCR was conducted according to the program shown in the following Table 10.

TABLE 10

| Temperature (° C.) | Reaction time (min) | cycle |
|---|---|---|
| 95 | 3 | — |
| 98 | 0.5 | 5 |
| 50 | 0.5 | |
| 70 | 0.5 | |
| 98 | 0.1 | — |
| 72 | 0.5 | 25 |
| 70 | 0.5 | |
| 70 | 7 | |
| 4 | — | — |

(5-2) Electrophoresis
Electrophoresis of the PCR reaction mixture was conducted with 1.2% PAGE at applied voltage of 100V for 30 minutes. The colonies of which amplification were confirmed were inoculated into the culture bottle containing LB liquid medium (manufactured by TOYOBO Co., LTD.) and incubated at 37° C.
(6) Purification of Plasmid
The plasmid in E. coli cultured in the LB liquid medium was purified by using Wizard Plus SV Minipreps. DNA Purification System (manufactured by Promega Co.) according the instruction attached thereto. After that, the sequences of the purified plasmid were sent to Eurofin Genomics Co., Ltd. for their analysis.
(7) Transformation of E. coli BL (DE3)
Ten μL of E. coli BL (DE3) competent cells (manufactured by BioDynamics Laboratory) were thawed on ice immediately before use, and prepared the competent cell solution. One μl of the plasmid solution, which was confirmed to contain the target sequence by the sequencing, was added to the competent cell solution, and left to stand on ice for 30 minutes.
After that, the solution was incubated at 42° C. for 30 seconds and then cooled on ice for 2 minutes. 90 μL of SOC medium (manufactured by TOYOBO Co., LTD.) was added to the solution, and reacted on a shaker at 37° C. for 1 hour. Thereafter, it was seeded on LB selection medium supplemented with ampicillin, and left to stand overnight at 37° C. Next day, transformed colonies emitting green fluorescence were collected, and inoculated into culture bottles containing 1 ml of LB liquid medium supplemented with ampicillin. Then, they were left to stand overnight at 37° C. for pre-culture.
(8) Purification of the Fluorescent Protein Binding to the Target Peptide Sequence
(8-1) Colony Cultivation
For samples, 4 tubes in 50 mL size to which both of 4 ml of the LB liquid medium supplemented with ampicillin and 290 μL, of the pre-cultured solutions were added were prepared, and cultured on the shaker at 28° C. for 4 hours. After that, 43 μL of 100 mM IPTG (isopropyl-β-thiogalactopyranoside) was added to them, and they were cultured overnight at 28° C. on the shaker.
(8-2) Recovery of the Protein
Next day, the cultures in the four tubes were collected into one tube. Three tubes of which contents were transferred were washed with 1 ml PBS (−) buffer (manufactured by Wako Pure Chemical Industry, Ltd.), and the washed solutions were also added to the collected tube to which the cultures were collected. The collected tube was centrifuged at room temperature for 5 minutes at 5,000 rpm (the name of centrifuge: KUBOTA3740, the rotor number: KUBOTA AF2018, manufactured by KUBOTA Co.)
After that, (i) the supernatant was discarded, and 3 ml of PBS (−) buffer was added to the precipitation pellet, (ii) to vortex well, and then the tube was centrifuged at 5,000 rpm for 5 minutes. The steps (i) and (ii) were repeated twice. Four ml of B-PER Lysis Buffer (manufactured by Reagent) was added to the precipitation pellet, and it was capped and stirred overnight at room temperature on the shaker.
(8-3) Purification by His-Tag
Two ml of Ni-NTA Agarose (manufactured by QIAGEN) was put in 15 ml tube, (i) the tube was centrifuged at 1,000 rpm for 1 minute, (ii) the supernatant was discarded, and 1× PBS buffer was added to the tube and vortexed well. The steps (i) and (ii) were repeated three times for preparing Ni-NTA resin.
The tube containing B-PER Lysis buffer solution was centrifuged at 12,000 rpm for 10 minutes at room temperature, and then the supernatant was transferred to a 15 ml Falcon tube. 400 μL of well stirred Ni-NTA resin was added to the tube, and then the tube was stirred at room temperature for 10 minutes by using the rotary shaker. After that, the tube was centrifuged at 1,000 rpm for 1 minute at room temperature, and the supernatant was discarded. (iii) 4 mL of 1× PBS buffer was added to the tube, and vortexed well, (iv) the tube was centrifuged at 1,000 rpm for 1 minute at room temperature, and the supernatant was discarded. The steps (iii) and (iv) were repeated twice.
After that, (v) 4 ml of 20 mM imidazole (manufactured by Wako Pure Chemical Industry, Ltd.) was added to the tube and vortexed well, (vi) the tube was centrifuged at 1,000 rpm for 1 minute at room temperature, and the supernatant was removed. The steps (v) and (vi) were repeated twice. 500 μl of 250 mM imidazole was added to the tube, and was stirred at room temperature for 10 minutes with the rotary shaker. Thereafter, the tube was centrifuged at 1,000 rpm for 1 minute, and the supernatant emitting green fluorescence was transferred to a new 15 ml Falcon tube to prepare the protein purified solution for the gel filtration in next stage.
(8-4) Purification by Gel Filtration
Imidazole in the protein purified solution was exchanged with PBS and the solution was purified to obtain the target peptide sequence binding fluorescent protein of interest. In the procedures described above, Nap5 column manufactured by GE Heath Care Japan KK. was used to conduct the purification according to the instruction attached thereto.

(9) Selection of the Target Peptide Sequence Binding Fluorescent Protein

The concentration of the target peptide sequence binding fluorescent protein obtained from the purification procedure was measures by using absorbance, 280 nm, and the chromophore concentration (chromophore forming ability) was measured by using absorbance, 488 nm, according to the conventional method. The proteins of which ratio of A488/A280 exceeded 1.5 were selected as the target peptide sequence binding fluorescent protein of the interest. The result was shown in Table 11.

TABLE 11

|  | Wavelength (nm) | | ratio |
|---|---|---|---|
| Absorbance | 280 | 488 | 488/280 |
| Sample 1 | 0.2459 | 0.5246 | 2.1335 |
| Sample 2 | 0.2487 | 0.5295 | 2.1289 |
| Sample 3 | 0.2494 | 0.5307 | 2.1280 |

Example 3

Preparation of the Target Peptide Sequence-Binding Micelle (Associated Fluorescent Protein Driving Type Micelle)

Instead of GFP, the target peptide sequence binding fluorescent protein prepared in the example 2 was used to form the micelles to which target peptide sequences were bound, an associated fluorescent protein driving micelle, as the same as those employed in the example 1.

(1) Emission Properties

Figure 10:
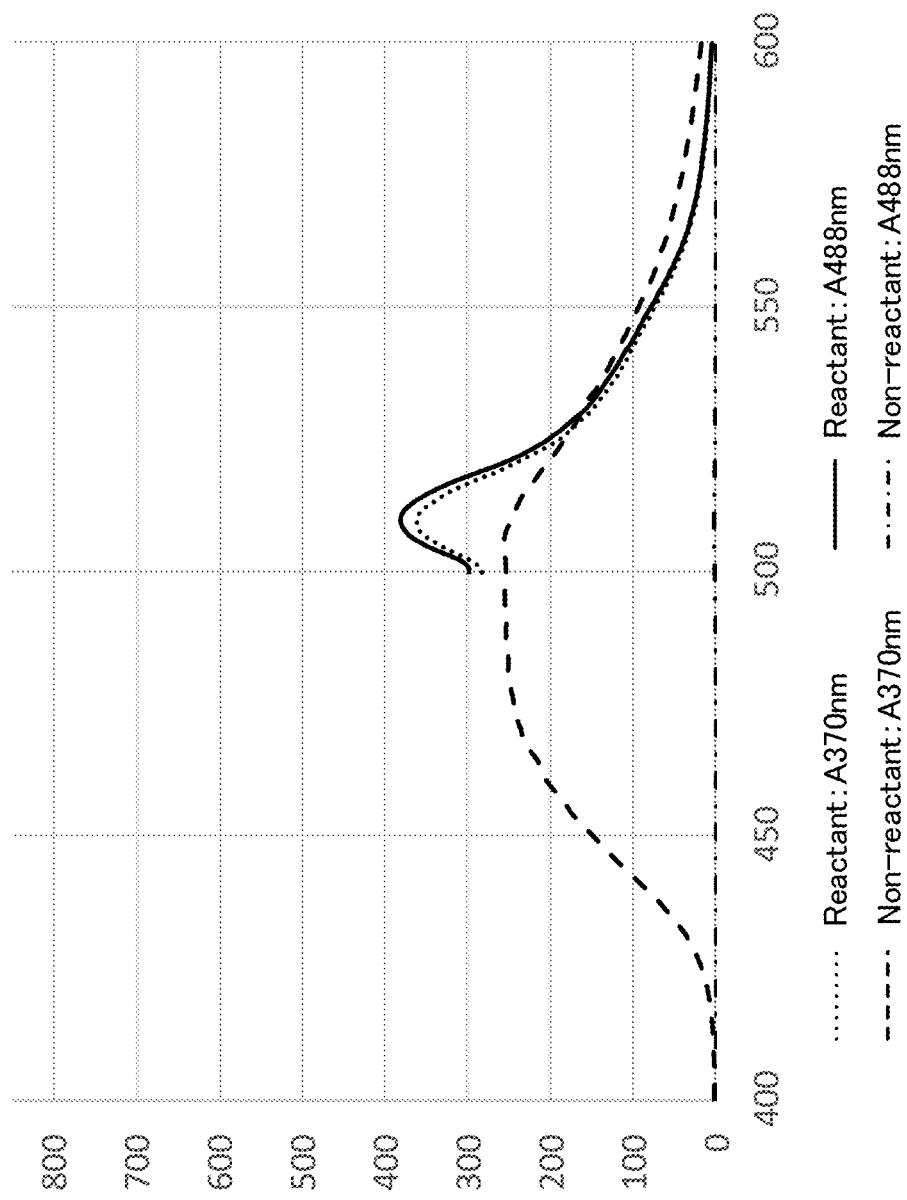
FIG. 10 is the graph showing the measuring result of the fluorescent spectrum of aggregated fluorescent protein driven micelle to which the target peptide sequence is bound.

The emission properties of the associated fluorescent protein driving micelle with target peptide sequence binding fluorescent protein prepared as described above were measured in the same way as in the example 1 (see FIG. 10). In the legend of FIG. 10, the reactant shows the complex of the silole dendrimer and the target peptide sequence binding fluorescent protein, the unreacted material shows those without them, and each number shows the wavelength of excitation light (nm). An emission peak was also observed around 510 nm in the target peptide sequence-binding micelle as the same as that in the example 1.

Figure 11:
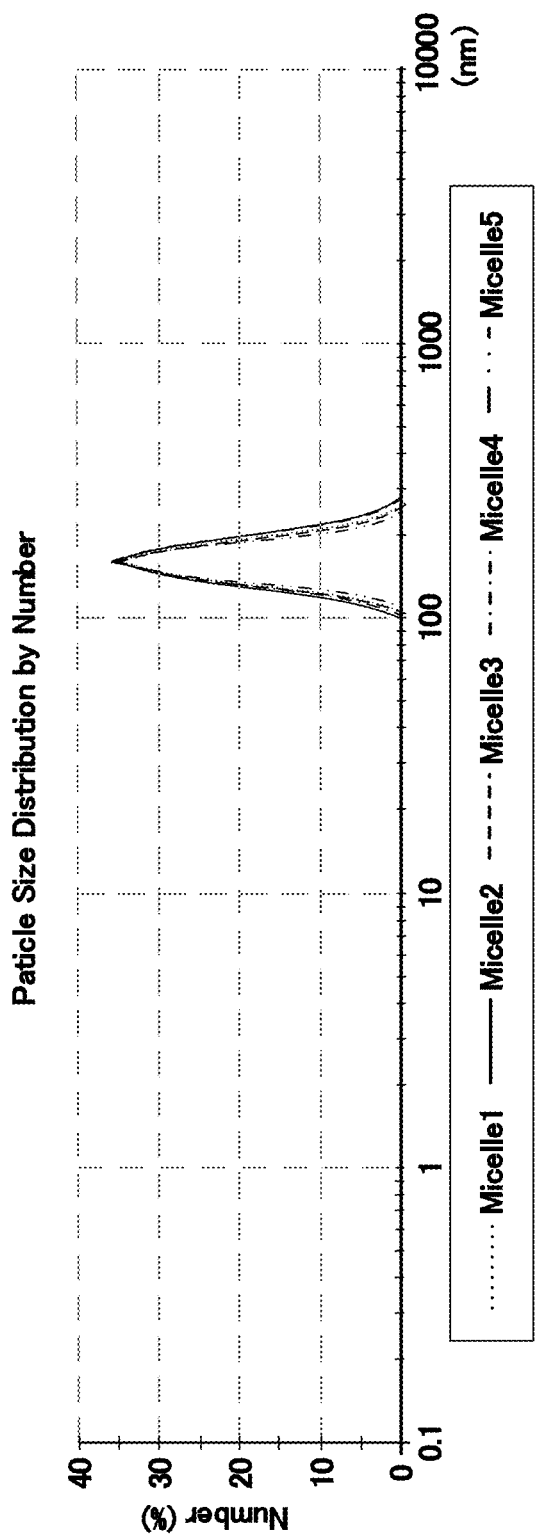
FIG. 11 is the graph showing the particle size distribution of aggregated fluorescent protein driven micelle to which the target peptide sequence of MCF-7 is bound.

The particle properties of the target peptide sequence-binding micelle were measured by a dynamic light scattering method as the same as used in the example 1 (see FIG. 11).

In FIG. 11, the horizontal axis shows the particle size of the obtained micelle, and the vertical axis shows the percentage of in the micelle size in whole micelle size shown in horizontal axis. As a result, the particles having the particle size of about 100 nm to 200 nm were confirmed as the same as those in the example 1.

From the above, it was demonstrated that the fluorescent protein-binding micelles having the target peptide sequence formed the equivalent size micelle to those without the target sequence. Furthermore, it was estimated that both of the micelles obtained in the example 1 and the present example were associated fluorescent protein driving type micelle.

INDUSTRIAL APPLICABILITY

The present invention is useful in the field of the pharmaceutical preparations, particularly in the field of drug delivery.

FREE TEXT OF SEQUENCE LISTING

SEQ ID NO: 1: Amino acid sequence of GFP
SEQ ID NO: 2: Amino acid sequence of GFP
SEQ ID NO: 3: Amino acid sequence of BFP
SEQ ID NO: 4: Amino acid sequence of YFP
SEQ ID NO: 5: Amino acid sequence of fluorescent protein derived from Discosoma
SEQ ID NO: 6: MCF-7 recognizing peptide sequence
SEQ ID NO: 7: Forward primer for inverse PCR
SEQ ID NO: 8: Reverse primer for inverse PCR
SEQ ID NO: 9: Forward primer for inverse PCR
SEQ ID NO: 10: Reverse primer for inverse PCR
SEQ ID NO: 11: Primer for inverse PCR
SEQ ID NO: 12: Primer for inverse PCR
SEQ ID NO: 13: Oligonucleotide
SEQ ID NO: 14: Oligonucleotide
SEQ ID NO: 15: Oligonucleotide
SEQ ID NO: 16: Oligonucleotide
SEQ ID NO: 17: Forward primer for inverse PCR
SEQ ID NO: 18: Reverse primer for inverse PCR
SEQ ID NO: 19: Forward primer for inverse PCR
SEQ ID NO: 20: Reverse primer for inverse PCR
SEQ ID NO: 21: Forward primer for inverse PCR
SEQ ID NO: 22: Forward primer for inverse PCR
SEQ ID NO: 23: Forward primer for inverse PCR
SEQ ID NO: 24: Reverse primer for inverse PCR
SEQ ID NO: Reverse primer for inverse PCR
SEQ ID NO: 26: Base sequence of plasmid for inverse PCR

The invention claimed is:

1. An aggregatable carrier material for a drug delivery system comprising an aggregatable dendrimer compound shown in formula (I):

[Chemical formula 1]

   (I)

wherein in the formula (I), $R^1$ is silole group shown in the following formula (II); each of $R^2$ and $R^3$ is a hydrocarbon chain having 1 to 6 carbon atoms which may have the same or a different hydrocarbon chain or a ring; Y is a halogen group or a targeted sequence presented part (TSPP) bound via a sulfur atom wherein at least one of Y is a TSPP; and

[Chemical formula 2]

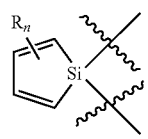

wherein R is a phenyl group; and n is 4 in the formula (II); wherein the targeted sequence presented part (TSPP) comprises a protein having a targeted recognition site of which said sulfur atom in said protein is located outside the folded protein; and wherein said targeted sequence presented part aggregates in an aqueous solvent to form a micelle having the diameter from 50 to 500 nm, and when said aggregatable molecule aggregates, said aggregated micelles emit fluorescence.

2. The aggregatable carrier material for a drug delivery system according to claim 1, wherein said compound shown in formula (I) is that shown in the following formula (III), and wherein n is an integer from 1 to 3, X is a bromine atom or —S-TSPP, and all X are not bromine atoms;

[Chemical formula 3]

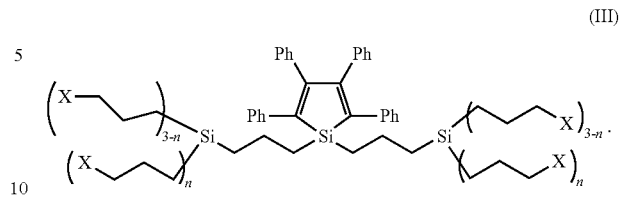

(III)

3. The aggregatable carrier material for drug delivery system according to claim 1, wherein said aggregatable molecule shown in the formula (I) is selected from the group consisting of the following formulae (IV) to (IX);

[Chemical formula 4]

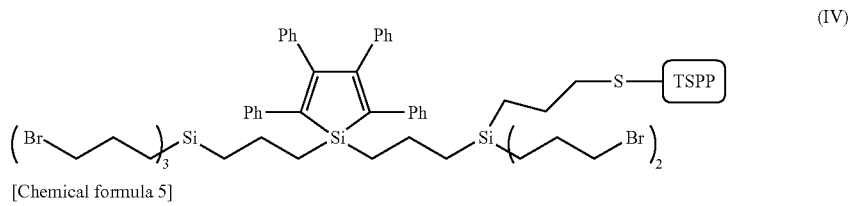

(IV)

[Chemical formula 5]

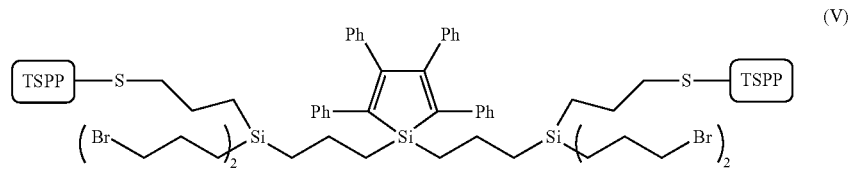

(V)

[Chemical formula 6]

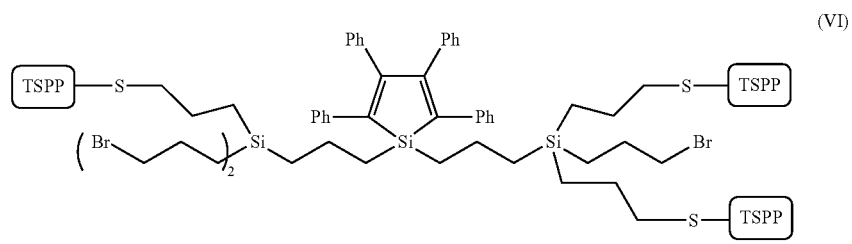

(VI)

[Chemical formula 7]

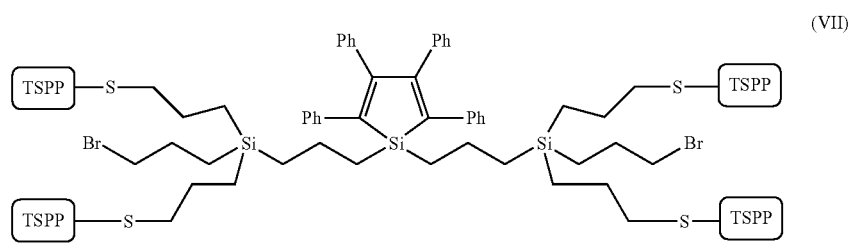

(VII)

[Chemical formula 8]

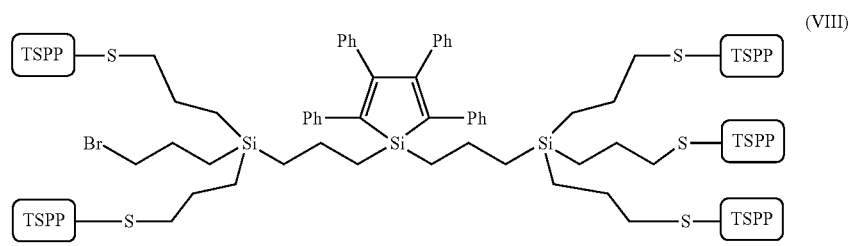

(VIII)

[Chemical formula 9]

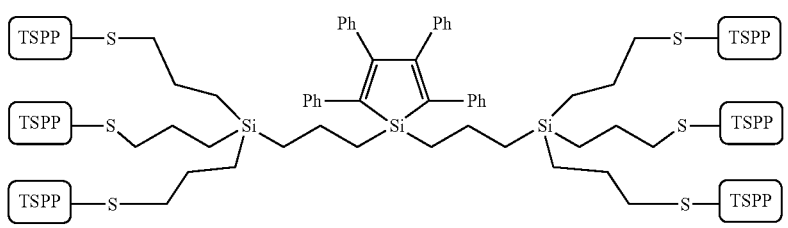

(IX)

wherein TSPP is the targeted sequence presented part in the formulae.

4. The aggregatable carrier material for drug delivery system according to claim 1, wherein the protein having said targeted recognition site is any one of fluorescent proteins selected from the group consisting of a white fluorescent protein, a red fluorescent protein, a yellow fluorescent protein, a blue fluorescent protein and a green fluorescent protein.

5. The aggregatable carrier material for drug delivery system according to claim 1, wherein said targeted recognition site is a functional peptide to deliver said micelle formed by said aggregatable carrier material to a targeted tissue.

6. The aggregatable carrier material for drug delivery system according to claim 5, wherein said targeted tissue is any one of a tissue selected from the group consisting of a normal tissue having inflammation, a tissue having undesirable gene expressions, a cell having the undesirable gene expressions, and a tissue composed of premalignant cells and tumor cells.

7. The aggregatable carrier material for drug delivery system according to claim 5, wherein said functional peptide specifically binds to any targeted protein selected from the group consisting of a surface antigen, a receptor, a gate, a transporter and a channel to form a conjugate for promoting endocytosis of said conjugate composed of said protein and said functional peptide into a cell.

8. A micelle formed by said aggregatable carrier material for drug delivery system according to claim 1, which encapsulates any one of the molecules selected from the group consisting of a protein having molecular weight of 200,000 or less, a nucleic acid and hydrophobic molecule.

9. The micelle according to claim 8, wherein said protein having the molecular weight of 200,000 or less is selected from the group consisting of immunoglobulin G, lectins, and peptide hormones.

* * * * *

SEQUENCE LISTING

```
<160> NUMBER OF SEQ ID NOS: 26

<210> SEQ ID NO 1
<211> LENGTH: 263
<212> TYPE: PRT
<213> ORGANISM: Artificial Sequence
<220> FEATURE:
<223> OTHER INFORMATION: GFP derived from Discosoma sp.
<220> FEATURE:
<221> NAME/KEY: MISC_FEATURE
<222> LOCATION: (1)..(263)

<400> SEQUENCE: 1
```

```
Met Ala Ser Met Thr Gly Gly Gln Gln Met Gly Arg Met Ser Lys Gly
1               5                   10                  15

Glu Glu Leu Phe Thr Gly Val Val Pro Ile Leu Val Glu Leu Asp Gly
            20                  25                  30

Asp Val Asn Gly His Lys Phe Ser Val Ser Gly Glu Gly Glu Gly Asp
        35                  40                  45

Ala Thr Tyr Gly Lys Leu Thr Leu Lys Phe Ile Ser Thr Thr Gly Lys
50                  55                  60

Leu Pro Val Pro Trp Pro Thr Leu Val Thr Thr Leu Thr Tyr Gly Val
65                  70                  75                  80

Gln Cys Phe Ser Arg Tyr Pro Asp His Met Lys Arg His Asp Phe Phe
                85                  90                  95

Lys Ser Ala Met Pro Glu Gly Tyr Val Gln Glu Arg Thr Ile Ser Phe
            100                 105                 110

Lys Asp Asp Gly Asn Tyr Lys Thr Arg Ala Glu Val Lys Phe Glu Gly
        115                 120                 125

Asp Thr Leu Val Asn Arg Ile Glu Leu Lys Gly Ile Asp Phe Lys Glu
    130                 135                 140

Asp Gly Asn Ile Leu Gly His Lys Leu Glu Tyr Asn Tyr Asn Ser His
145                 150                 155                 160

Asn Val Tyr Ile Thr Ala Asp Lys Gln Lys Asn Gly Ile Lys Ala Asn
                165                 170                 175

Phe Lys Thr Arg His Asn Ile Glu Asp Gly Ser Val Gln Leu Ala Asp
            180                 185                 190

His Tyr Gln Gln Asn Thr Pro Ile Gly Asp Gly Pro Val Leu Leu Pro
        195                 200                 205

Asp Asn His Tyr Leu Ser Thr Gln Ser Ala Leu Leu Lys Asp Pro Asn
    210                 215                 220

Glu Lys Arg Asp His Met Val Leu Leu Glu Phe Val Thr Ala Ala Gly
225                 230                 235                 240

Ser Gly Ile Thr Asp Glu Val Asp Gly Thr Cys Glu Leu Tyr Lys Gly
                245                 250                 255

Gly His His His His His
            260

<210> SEQ ID NO 2
<211> LENGTH: 258
<212> TYPE: PRT
<213> ORGANISM: Artificial Sequence
<220> FEATURE:
<223> OTHER INFORMATION: GFP derived from Discosoma sp.
<220> FEATURE:
<221> NAME/KEY: MISC_FEATURE
<222> LOCATION: (1)..(258)

<400> SEQUENCE: 2

Met Ala Ser Met Thr Gly Gly Gln Gln Met Gly Arg Met Ser Lys Gly
1               5                   10                  15

Glu Glu Leu Phe Thr Gly Val Val Pro Ile Leu Val Glu Leu Asp Gly
            20                  25                  30

Asp Val Asn Gly His Lys Phe Ser Val Ser Gly Glu Gly Glu Gly Asp
        35                  40                  45

Ala Thr Tyr Gly Lys Leu Thr Leu Lys Phe Ile Cys Thr Thr Gly Lys
    50                  55                  60

Leu Pro Val Pro Trp Pro Thr Leu Val Thr Thr Leu Thr Tyr Gly Val
65                  70                  75                  80
```

```
Gln Cys Phe Ser Arg Tyr Pro Asp His Met Lys Arg His Asp Phe Phe
                 85                  90                  95
Lys Ser Ala Met Pro Glu Gly Tyr Val Gln Glu Arg Thr Ile Ser Phe
            100                 105                 110
Lys Asp Asp Gly Asn Tyr Lys Thr Arg Ala Glu Val Lys Phe Glu Gly
            115                 120                 125
Asp Thr Leu Val Asn Arg Ile Glu Leu Lys Gly Ile Asp Phe Lys Glu
            130                 135                 140
Asp Gly Asn Ile Leu Gly His Lys Leu Glu Tyr Asn Tyr Asn Ser His
145                 150                 155                 160
Asn Val Tyr Ile Thr Ala Asp Lys Gln Lys Asn Gly Ile Lys Ala Asn
                165                 170                 175
Phe Lys Thr Arg His Asn Ile Glu Asp Gly Ser Val Gln Leu Ala Asp
            180                 185                 190
His Tyr Gln Gln Asn Thr Pro Ile Gly Asp Gly Pro Val Leu Leu Pro
            195                 200                 205
Asp Asn His Tyr Leu Ser Thr Gln Ser Ala Leu Leu Lys Asp Pro Asn
210                 215                 220
Glu Lys Arg Asp His Met Val Leu Leu Glu Phe Val Thr Ala Ala Gly
225                 230                 235                 240
Ile Thr His Gly Met Asp Glu Leu Tyr Lys Gly Gly His His His His
                245                 250                 255
His His

<210> SEQ ID NO 3
<211> LENGTH: 259
<212> TYPE: PRT
<213> ORGANISM: Artificial Sequence
<220> FEATURE:
<223> OTHER INFORMATION: BFP derivedfrom Discosoma sp.
<220> FEATURE:
<221> NAME/KEY: MISC_FEATURE
<222> LOCATION: (1)..(259)

<400> SEQUENCE: 3

Met Ala Ser Met Thr Gly Gly Gln Gln Met Gly Arg Met Val Ser Lys
1               5                   10                  15
Gly Glu Glu Leu Phe Thr Gly Val Val Pro Ile Leu Val Glu Leu Asp
            20                  25                  30
Gly Asp Val Asn Gly His Lys Phe Ser Val Ser Gly Glu Gly Glu Gly
            35                  40                  45
Asp Ala Thr Tyr Gly Lys Leu Thr Leu Lys Phe Ile Cys Thr Thr Gly
        50                  55                  60
Lys Leu Pro Val Pro Trp Pro Thr Leu Val Thr Thr Leu Thr His Gly
65                  70                  75                  80
Val Gln Cys Phe Ser Arg Tyr Pro Asp His Met Lys Gln His Asp Phe
                85                  90                  95
Phe Lys Ser Ala Met Pro Glu Gly Tyr Val Gln Glu Arg Thr Ile Phe
            100                 105                 110
Phe Lys Asp Asp Gly Asn Tyr Lys Thr Arg Ala Glu Val Lys Phe Glu
            115                 120                 125
Gly Asp Thr Leu Val Asn Arg Ile Glu Leu Lys Gly Ile Asp Phe Lys
            130                 135                 140
Glu Asp Gly Asn Ile Leu Gly His Lys Leu Glu Tyr Asn Phe Asn Ser
145                 150                 155                 160
His Asn Val Tyr Ile Met Ala Asp Lys Gln Lys Asn Gly Ile Lys Val
```

-continued

```
                165                 170                 175
Asn Phe Lys Ile Arg His Asn Ile Glu Asp Gly Ser Val Gln Leu Ala
                180                 185                 190

Asp His Tyr Gln Gln Asn Thr Pro Ile Gly Asp Gly Pro Val Leu Leu
                195                 200                 205

Pro Asp Asn His Tyr Leu Ser Thr Gln Ser Ala Leu Ser Lys Asp Pro
    210                 215                 220

Asn Glu Lys Arg Asp His Met Val Leu Leu Glu Phe Val Thr Ala Ala
225                 230                 235                 240

Gly Ile Thr Leu Gly Met Asp Glu Leu Tyr Lys Gly Gly His His His
                245                 250                 255

His His His
```

<210> SEQ ID NO 4
<211> LENGTH: 259
<212> TYPE: PRT
<213> ORGANISM: Artificial Sequence
<220> FEATURE:
<223> OTHER INFORMATION: YFP derived from Discosoma sp.
<220> FEATURE:
<221> NAME/KEY: MISC_FEATURE
<222> LOCATION: (1)..(259)

<400> SEQUENCE: 4

```
Met Ala Ser Met Thr Gly Gly Gln Gln Met Gly Arg Met Val Ser Lys
1               5                   10                  15

Gly Glu Glu Leu Phe Thr Gly Val Val Pro Ile Leu Val Glu Leu Asp
                20                  25                  30

Gly Asp Val Asn Gly His Lys Phe Ser Val Ser Gly Glu Gly Glu Gly
                35                  40                  45

Asp Ala Thr Tyr Gly Lys Leu Thr Leu Lys Phe Ile Cys Thr Thr Gly
    50                  55                  60

Lys Leu Pro Val Pro Trp Pro Thr Leu Val Thr Thr Phe Gly Tyr Gly
65                  70                  75                  80

Leu Gln Cys Phe Ala Arg Tyr Pro Asp His Met Lys Gln His Asp Phe
                85                  90                  95

Phe Lys Ser Ala Met Pro Glu Gly Tyr Val Gln Glu Arg Thr Ile Phe
                100                 105                 110

Phe Lys Asp Asp Gly Asn Tyr Lys Thr Arg Ala Glu Val Lys Phe Glu
                115                 120                 125

Gly Asp Thr Leu Val Asn Arg Ile Glu Leu Lys Gly Ile Asp Phe Lys
    130                 135                 140

Glu Asp Gly Asn Ile Leu Gly His Lys Leu Glu Tyr Asn Tyr Asn Ser
145                 150                 155                 160

His Asn Val Tyr Ile Met Ala Asp Lys Gln Lys Asn Gly Ile Lys Val
                165                 170                 175

Asn Phe Lys Ile Arg His Asn Ile Glu Asp Gly Ser Val Gln Leu Ala
                180                 185                 190

Asp His Tyr Gln Gln Asn Thr Pro Ile Gly Asp Gly Pro Val Leu Leu
                195                 200                 205

Pro Asp Asn His Tyr Leu Ser Tyr Gln Ser Ala Leu Ser Lys Asp Pro
    210                 215                 220

Asn Glu Lys Arg Asp His Met Val Leu Leu Glu Phe Val Thr Ala Ala
225                 230                 235                 240

Gly Ile Thr Leu Gly Met Asp Glu Leu Tyr Lys Gly Gly His His His
                245                 250                 255
```

His His His

<210> SEQ ID NO 5
<211> LENGTH: 236
<212> TYPE: PRT
<213> ORGANISM: Artificial Sequence
<220> FEATURE:
<223> OTHER INFORMATION: GFP derived from Discosoma sp.
<220> FEATURE:
<221> NAME/KEY: MISC_FEATURE
<222> LOCATION: (1)..(236)

<400> SEQUENCE: 5

```
Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
            20                  25                  30

Gly Glu Gly Arg Pro Tyr Glu Gly Thr Gln Thr Ala Lys Leu Lys Val
        35                  40                  45

Thr Lys Gly Gly Pro Leu Pro Phe Ala Trp Asp Ile Leu Ser Pro Gln
50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
130                 135                 140

Pro Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
210                 215                 220

Leu Gly Thr Cys Gly Gly His His His His His
225                 230                 235
```

<210> SEQ ID NO 6
<211> LENGTH: 8
<212> TYPE: PRT
<213> ORGANISM: Artificial Sequence
<220> FEATURE:
<223> OTHER INFORMATION: Peptide tag for targeting MCF-7 cell
<220> FEATURE:
<221> NAME/KEY: MISC_FEATURE
<222> LOCATION: (1)..(8)

<400> SEQUENCE: 6

```
Asp Met Pro Gly Thr Val Leu Pro
1               5
```

<210> SEQ ID NO 7

```
<211> LENGTH: 45
<212> TYPE: DNA
<213> ORGANISM: Artificial Sequence
<220> FEATURE:
<223> OTHER INFORMATION: Forward primer for MCF-7 cell by using Inverse
      PCR
<220> FEATURE:
<221> NAME/KEY: primer_bind
<222> LOCATION: (1)..(45)

<400> SEQUENCE: 7
cctggtactg ttcttcctgg tggtatgagt aaaggagaag aactt              45

<210> SEQ ID NO 8
<211> LENGTH: 27
<212> TYPE: DNA
<213> ORGANISM: Artificial Sequence
<220> FEATURE:
<223> OTHER INFORMATION: Reverse primer for MCF-7 cell by using Inverse
      PCR
<220> FEATURE:
<221> NAME/KEY: primer_bind
<222> LOCATION: (1)..(27)

<400> SEQUENCE: 8
catatcgcga cccatttgct gtccacc                                  27

<210> SEQ ID NO 9
<211> LENGTH: 22
<212> TYPE: DNA
<213> ORGANISM: Artificial Sequence
<220> FEATURE:
<223> OTHER INFORMATION: Forward primer for preparing a construct,
      pGFPgcn5
<220> FEATURE:
<221> NAME/KEY: primer_bind
<222> LOCATION: (1)..(22)

<400> SEQUENCE: 9
cattgaagat ggctccgttc aa                                       22

<210> SEQ ID NO 10
<211> LENGTH: 22
<212> TYPE: DNA
<213> ORGANISM: Artificial Sequence
<220> FEATURE:
<223> OTHER INFORMATION: Reverse primer for preparing GFPuv5
<220> FEATURE:
<221> NAME/KEY: primer_bind
<222> LOCATION: (1)..(22)

<400> SEQUENCE: 10
ttgtggcgag ttttgaagtt ag                                       22

<210> SEQ ID NO 11
<211> LENGTH: 70
<212> TYPE: DNA
<213> ORGANISM: Artificial Sequence
<220> FEATURE:
<223> OTHER INFORMATION: Forward primer for amplifying code region of
      GFPuv5tag
<220> FEATURE:
<221> NAME/KEY: primer_bind
<222> LOCATION: (1)..(70)

<400> SEQUENCE: 11
ctcgaccata tggctagcat gactggtgga cagcaaatgg gtcgcatgag taaaggagaa  60
gaacttttca                                                       70
```

<210> SEQ ID NO 12
<211> LENGTH: 54
<212> TYPE: DNA
<213> ORGANISM: Artificial Sequence
<220> FEATURE:
<223> OTHER INFORMATION: Reverse primer for amplifying code region of
      GFPuv5tag
<220> FEATURE:
<221> NAME/KEY: primer_bind
<222> LOCATION: (1)..(54)

<400> SEQUENCE: 12
tgacgtgaat tcattagtga tggtgatggt gatgtttgta gagctcatcc atgc        54

<210> SEQ ID NO 13
<211> LENGTH: 25
<212> TYPE: DNA
<213> ORGANISM: Artificial Sequence
<220> FEATURE:
<223> OTHER INFORMATION: Primer for preparing oligonucleotide with Cys
      48 mutation of GFPuv5tag by using for inverse PCR
<220> FEATURE:
<221> NAME/KEY: misc_feature
<222> LOCATION: (1)..(25)
<220> FEATURE:
<221> NAME/KEY: misc_feature
<222> LOCATION: (13)..(14)
<223> OTHER INFORMATION: n is a, c, g, or t

<400> SEQUENCE: 13
cttaaattta ttnnkactgg aaaac                                        25

<210> SEQ ID NO 14
<211> LENGTH: 20
<212> TYPE: DNA
<213> ORGANISM: Artificial Sequence
<220> FEATURE:
<223> OTHER INFORMATION: Primer for preparing oligonucleotide with Cys
      48 mutation of GFPuv5tag by using for inverse PCR
<220> FEATURE:
<221> NAME/KEY: primer_bind
<222> LOCATION: (1)..(20)

<400> SEQUENCE: 14
ggtaagtttt ccgtatgttg                                              20

<210> SEQ ID NO 15
<211> LENGTH: 26
<212> TYPE: DNA
<213> ORGANISM: Artificial Sequence
<220> FEATURE:
<223> OTHER INFORMATION: Primer for preparing oligonucleotide with Cys
      70 mutation of GFPuv5tag by using for inverse PCR
<220> FEATURE:
<221> NAME/KEY: primer_bind
<222> LOCATION: (1)..(26)
<223> OTHER INFORMATION: n is a, c, g, or t.  k is  g or t.
<220> FEATURE:
<221> NAME/KEY: misc_feature
<222> LOCATION: (9)..(10)
<223> OTHER INFORMATION: n is a, c, g, or t

<400> SEQUENCE: 15
gtgttcaann kttttcccgt tatccg                                       26

<210> SEQ ID NO 16
<211> LENGTH: 22
<212> TYPE: DNA
<213> ORGANISM: Artificial Sequence
<220> FEATURE:

```
<223> OTHER INFORMATION: Primer for preparing oligonucleotide with Cys
      70 mutation of GFPuv5tag by using for inverse PCR
<220> FEATURE:
<221> NAME/KEY: primer_bind
<222> LOCATION: (1)..(22)

<400> SEQUENCE: 16
catacgtcag agtagtgaca ag                                              22

<210> SEQ ID NO 17
<211> LENGTH: 23
<212> TYPE: DNA
<213> ORGANISM: Artificial Sequence
<220> FEATURE:
<223> OTHER INFORMATION: Forward primer for preparing oligonucleotide
      with Cys-double mutation of GFPuv5tag by using for inverse PCR
<220> FEATURE:
<221> NAME/KEY: primer_bind
<222> LOCATION: (1)..(23)

<400> SEQUENCE: 17
tgtcttttca ctggagttgt ccc                                             23

<210> SEQ ID NO 18
<211> LENGTH: 21
<212> TYPE: DNA
<213> ORGANISM: Artificial Sequence
<220> FEATURE:
<223> OTHER INFORMATION: Primer for preparing oligonucleotide with
      Cys-double mutation of GFPuv5tag by using for inverse PCR
<220> FEATURE:
<221> NAME/KEY: primer_bind
<222> LOCATION: (1)..(21)

<400> SEQUENCE: 18
ttctccttta ctcatttttt c                                               21

<210> SEQ ID NO 19
<211> LENGTH: 24
<212> TYPE: DNA
<213> ORGANISM: Artificial Sequence
<220> FEATURE:
<223> OTHER INFORMATION: Forward primer for preparing oligonucleotide
      with Cys-mutation of GFPuv5tag by using for inverse PCR
<220> FEATURE:
<221> NAME/KEY: primer_bind
<222> LOCATION: (1)..(24)

<400> SEQUENCE: 19
tgcacacatg gcatggatga gctc                                            24

<210> SEQ ID NO 20
<211> LENGTH: 21
<212> TYPE: DNA
<213> ORGANISM: Artificial Sequence
<220> FEATURE:
<223> OTHER INFORMATION: Primer for preparing oligonucleotide with
      Cys-mutation of GFPuv5tag by using for inverse PCR
<220> FEATURE:
<221> NAME/KEY: primer_bind
<222> LOCATION: (1)..(21)

<400> SEQUENCE: 20
cccagcagca gttacaaact c                                               21

<210> SEQ ID NO 21
<211> LENGTH: 33
<212> TYPE: DNA
<213> ORGANISM: Artificial Sequence
```

-continued

```
<220> FEATURE:
<223> OTHER INFORMATION: Forward primer for pUV5trypS0tag
<220> FEATURE:
<221> NAME/KEY: primer_bind
<222> LOCATION: (1)..(33)

<400> SEQUENCE: 21
cagcgccgtt gtgagctcta caaataatga att                                    33

<210> SEQ ID NO 22
<211> LENGTH: 21
<212> TYPE: DNA
<213> ORGANISM: Artificial Sequence
<220> FEATURE:
<223> OTHER INFORMATION: Forward primer for pUV5trypS1tag
<220> FEATURE:
<221> NAME/KEY: primer_bind
<222> LOCATION: (1)..(21)

<400> SEQUENCE: 22
acatgtgagc tctacaaata a                                                 21

<210> SEQ ID NO 23
<211> LENGTH: 21
<212> TYPE: DNA
<213> ORGANISM: Artificial Sequence
<220> FEATURE:
<223> OTHER INFORMATION: Forward primer for pUV5trypS2tag
<220> FEATURE:
<221> NAME/KEY: primer_bind
<222> LOCATION: (1)..(21)

<400> SEQUENCE: 23
ggaacatgtg agctctacaa a                                                 21

<210> SEQ ID NO 24
<211> LENGTH: 21
<212> TYPE: DNA
<213> ORGANISM: Artificial Sequence
<220> FEATURE:
<223> OTHER INFORMATION: Reverse primer for pUV5trypS0tag
<220> FEATURE:
<221> NAME/KEY: primer_bind
<222> LOCATION: (1)..(21)

<400> SEQUENCE: 24
tgtaatccca gcagcagtta c                                                 21

<210> SEQ ID NO 25
<211> LENGTH: 18
<212> TYPE: DNA
<213> ORGANISM: Artificial Sequence
<220> FEATURE:
<223> OTHER INFORMATION: Forward primer both for pUV5trypS1tag &
      pUV5trypS2tag
<220> FEATURE:
<221> NAME/KEY: primer_bind
<222> LOCATION: (1)..(18)

<400> SEQUENCE: 25
acggccctgt gtaatccc                                                     18

<210> SEQ ID NO 26
<211> LENGTH: 6194
<212> TYPE: DNA
<213> ORGANISM: Artificial Sequence
<220> FEATURE:
<223> OTHER INFORMATION: Nucleotide sequence of a plasmid for inverse
      PCR
```

```
<220> FEATURE:
<221> NAME/KEY: misc_structure
<222> LOCATION: (1)..(6194)

<400> SEQUENCE: 26
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tcccttagg      180 gttccgattt agtgctttac ggcacctcga ccccaaaaaa cttgattagg gtgatggttc     240
acgtagtggg ccatcgccct gatagacggt ttttcgccct tgacgttgg agtccacgtt      300 ctttaatagt ggactcttgt tccaaactgg aacaacactc aaccctatct cggtctattc     360
ttttgattta taggatttt tgccgatttc ggcctattgg ttaaaaaatg agctgattta     420
acaaaatttt aacgcgaatt ttaacaaaat attaacgttt acaatttcag gtggcacttt     480
tcggggaaat gtgcgcggaa cccctatttg tttatttttc taaatacatt caaatatgta     540
tccgctcatg agacaataac cctgataaat gcttcaataa tattgaaaaa ggaagagtat     600
gagtattcaa catttccgtg tcgcccttat tcccttttt gcggcatttt gccttcctgt      660
ttttgctcac ccagaaacgc tggtgaaagt aaaagatgct gaagatcagt tgggtgcacg     720
agtgggttac atcgaactgg atctcaacag cggtaagatc cttgagagtt ttcgccccga     780
agaacgtttt ccaatgatga gcacttttaa agttctgcta tgtggcgcgg tattatcccg     840
tattgacgcc gggcaagagc aactcggtcg ccgcatacac tattctcaga atgacttggt      900
tgagtactca ccagtcacag aaaagcatct tacggatggc atgacagtaa gagaattatg      960
cagtgctgcc ataaccatga gtgataacac tgcggccaac ttacttctga acgatcgg     1020 aggaccgaag gagctaaccg cttttttgca acatggggg atcatgtaa ctcgccttga     1080 tcgttgggaa ccggagctga atgaagccat accaaacgac gagcgtgaca ccacgatgcc     1140
tgcagcaatg gcaacaacgt tgcgcaaact attaactggc gaactactta ctctagcttc     1200
ccggcaacaa ttaatagact ggatggaggc ggataaagtt gcaggaccac ttctgcgctc     1260
ggcccttccg gctggctggt ttattgctga taaatctgga gccggtgagc gtgggtctcg     1320
cggtatcatt gcagcactgg ggccagatgg taagccctcc cgtatcgtag ttatctacac     1380 gacgggagt caggcaacta tggatgaacg aaatagacag atcgctgaga taggtgcctc     1440
actgattaag cattggtaac tgtcagacca agtttactca tatatacttt agattgattt     1500
aaaacttcat ttttaattta aaaggatcta ggtgaagatc ctttttgata atctcatgac     1560
caaaatccct taacgtgagt tttcgttcca ctgagcgtca gaccccgtag aaaagatcaa     1620
aggatcttct tgagatcctt ttttttctgcg cgtaatctgc tgcttgcaaa caaaaaaacc     1680
accgctacca gcggtggttt gtttgccgga tcaagagcta ccaactcttt ttccgaaggt     1740
aactggcttc agcagagcgc agataccaaa tactgtcctt ctagtgtagc cgtagttagg     1800
ccaccacttc aagaactctg tagcaccgcc tacatacctc gctctgctaa tcctgttacc     1860
agtggctgct gccagtggcg ataagtcgtg tcttaccggg ttggactcaa gacgatagtt     1920
accggataag gcgcagcggt cgggctgaac ggggggttcg tgcacacagc ccagcttgga     1980
gcgaacgacc tacaccgaac tgagatacct acagcgtgag ctatgagaaa gcgccacgct     2040
tcccgaaggg agaaaggcgg acaggtatcc ggtaagcggc agggtcggaa caggagagcg     2100
cacgagggag cttccagggg gaaacgcctg gtatctttat agtcctgtcg gtttcgcca     2160 cctctgactt gagcgtcgat ttttgtgatg ctcgtcaggg gggcggagcc tatggaaaaa     2220
```

```
cgccagcaac gcggccttt  tacggttcct ggccttttgc tggccttttg ctcacatgtt  2280
ctttcctgcg ttatcccctg attctgtgga taaccgtatt accgcctttg agtgagctga  2340
taccgctcgc cgcagccgaa cgaccgagcg cagcgagtca gtgagcgagg aagcggaaga  2400
gcgcctgatg cggtattttc tccttacgca tctgtgcggt atttcacacc gcatatatgg  2460
tgcactctca gtacaatctg ctctgatgcc gcatagttaa gccagtatac actccgctat  2520
cgctacgtga ctgggtcatg gctgcgcccc gacacccgcc aacacccgct gacgcgccct  2580
gacgggcttg tctgctcccg gcatccgctt acagacaagc tgtgaccgtc tccgggagct  2640
gcatgtgtca gaggttttca ccgtcatcac cgaaacgcgc gaggcagctg cggtaaagct  2700
catcagcgtg gtcgtgaagc gattcacaga tgtctgcctg ttcatccgcg tccagctcgt  2760
tgagtttctc cagaagcgtt aatgtctggc ttctgataaa gcgggccatg ttaagggcgg  2820
ttttttcctg tttggtcact gatgcctccg tgtaaggggg atttctgttc atggggtaa   2880 tgataccgat gaaacgagag aggatgctca cgatacgggt tactgatgat gaacatgccc  2940
ggttactgga acgttgtgag ggtaaacaac tggcggtatg gatgcggcgg gaccagagaa  3000
aaatcactca gggtcaatgc cagcgcttcg ttaatacaga tgtaggtgtt ccacagggta  3060
gccagcagca tcctgcgatg cagatccgga acataatggt gcagggcgct gacttccgcg  3120
tttccagact ttacgaaaca cggaaaccga agaccattca tgttgttgct caggtcgcag  3180
acgttttgca gcagcagtcg cttcacgttc gctcgcgtat cggtgattca ttctgctaac  3240
cagtaaggca accccgccag cctagccggg tcctcaacga caggagcacg atcatgcgca  3300
cccgtggggc cgccatgccg gcgataatgg cctgcttctc gccgaaacgt tggtggcgg   3360 gaccagtgac gaaggcttga gcgagggcgt gcaagattcc gaataccgca agcgacaggc  3420
cgatcatcgt cgcgctccag cgaaagcggt cctcgccgaa aatgacccag agcgctgccg  3480
gcacctgtcc tacgagttgc atgataaaga agacagtcat aagtgcggcg acgatagtca  3540
tgccccgcgc ccaccggaag gagctgactg ggttgaaggc tctcaagggc atcggtcgag  3600
atcccggtgc ctaatgagtg agctaactta cattaattgc gttgcgctca ctgcccgctt  3660
tccagtcggg aaacctgtcg tgccagctgc attaatgaat cggccaacgc gcggggagag  3720
gcggtttgcg tattgggcgc cagggtggtt tttcttttca ccagtgagac gggcaacagc  3780
tgattgccct tcaccgcctg gccctgagag agttgcagca agcggtccac gctggtttgc  3840
cccagcaggc gaaaatcctg tttgatggtg gttaacggcg ggatataaca tgagctgtct  3900
tcggtatcgt cgtatcccac taccgagata tccgcaccaa cgcgcagccc ggactcggta  3960
atggcgcgca ttgcgcccag cgccatctga tcgttggcaa ccagcatcgc agtgggaacg  4020
atgccctcat tcagcatttg catggtttgt tgaaaaccgg acatggcact ccagtcgcct  4080
tcccgttccg ctatcggctg aatttgattg cgagtgagat atttatgcca gccagccaga  4140
cgcagacgcg ccgagacaga acttaatggg cccgctaaca gcgcgatttg ctggtgaccc  4200
aatgcgacca gatgctccac gcccagtcgc gtaccgtctt catgggagaa ataatactg   4260 ttgatgggtg tctggtcaga gacatcaaga ataacgccg  gaacattagt gcaggcagct  4320
tccacagcaa tggcatcctg gtcatccagc ggatagttaa tgatcagccc actgacgcgt  4380
tgcgcgagaa gattgtgcac cgccgcttta caggcttcga cgccgcttcg ttctaccatc  4440
```

```
gacaccacca cgctggcacc cagttgatcg gcgcgagatt taatcgccgc gacaatttgc    4500
gacggcgcgt gcagggccag actggaggtg gcaacgccaa tcagcaacga ctgtttgccc    4560
gccagttgtt gtgccacgcg gttgggaatg taattcagct ccgccatcgc cgcttccact    4620
ttttcccgcg ttttcgcaga aacgtggctg gcctggttca ccacgcggga aacggtctga    4680
taagagacac cggcatactc tgcgacatcg tataacgtta ctggtttcac attcaccacc    4740
ctgaattgac tctcttccgg gcgctatcat gccataccgc gaaaggtttt gcgccattcg    4800
atggtgtccg ggatctcgac gctctccctt atgcgactcc tgcattagga agcagcccag    4860
tagtaggttg aggccgttga gcaccgccgc cgcaaggaat ggtgcatgca aggagatggc    4920
gcccaacagt cccccggcca cggggcctgc caccataccc acgccgaaac aagcgctcat    4980
gagcccgaag tggcgagccc gatcttcccc atcggtgatg tcggcgatat aggcgccagc    5040
aaccgcacct gtggcgccgg tgatgccggc cacgatgcgt ccggcgtaga ggatcgagat    5100
ctcgatcccg cgaaattaat acgactcact atagggaat tgtgagcgga taacaattcc    5160
cctctagaaa taattttgtt aactttaag aaggagatat acatatggct agcatgactg    5220
gtggacagca aatgggtcgc atgagtaaag gagaagaact tttcactgga gttgtcccaa    5280
ttcttgttga attagatggt gatgttaatg ggcacaaatt ttctgtcagc ggagagggtg    5340
aaggtgatgc aacatacgga aaacttaccc ttaaatttat ttctactact ggaaaactac    5400
ctgttccatg gccaacactt gtcactactc tgacgtatgg tgttcaatgc ttttcccgtt    5460
atccggatca catgaaacgg catgactttt tcaagagtgc catgcccgaa ggttatgtac    5520
aggaacgcac tatatctttc aaagatgacg ggaactacaa gacgcgtgct gaagtcaagt    5580
ttgaaggtga taccttgtt aatcgtatcg agttaaaagg tattgatttt aaagaagatg    5640
gaaacattct cggacacaaa ctcgagtaca actataactc acacaatgta tacatcacgg    5700
cagacaaaca aaagaatgga atcaaagcta acttcaaaac tcgccacaac attgaagatg    5760
gctccgttca actagcagac cattatcagc aaaatactcc aattggcgat ggccctgtcc    5820
ttttaccaga caaccattac ctgtcgacac aatctgccct tttgaaagat cccaacgaaa    5880
agcgtgacca catggtcctt cttgagtttg taactgctgc tgggtcaggg attacagatg    5940
aagtagatgg aacatgtgag ctctacaaag gtggccatca ccatcaccat cactaatgaa    6000
ttcgagctcc gtcgacaagc ttgcggccgc actcgagcac caccaccacc accactgaga    6060
tccggctgct aacaaagccc gaaaggaagc tgagttggct gctgccaccg ctgagcaata    6120
actagcataa ccccttgggg cctctaaacg ggtcttgagg ggttttttgc tgaaaggagg    6180
aactatatcc ggat                                                     6194
```